US008877482B2

(12) United States Patent
Lee et al.

(10) Patent No.: US 8,877,482 B2
(45) Date of Patent: Nov. 4, 2014

(54) HOMO-SUCCINIC ACID PRODUCING MICROORGANISM VARIANT AND PROCESS FOR PREPARING SUCCINIC ACID USING THE SAME

(75) Inventors: Sang Yup Lee, Daejeon (KR); Ji Mahn Kim, Seoul (KR); Jeong Wook Lee, Daejeon (KR); Hyohak Song, Daejeon (KR); Sol Choi, Jeju-do (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 597 days.

(21) Appl. No.: 12/668,868

(22) PCT Filed: Jan. 15, 2008

(86) PCT No.: PCT/KR2008/000241
§ 371 (c)(1),
(2), (4) Date: Jan. 12, 2010

(87) PCT Pub. No.: WO2009/008574
PCT Pub. Date: Jan. 15, 2009

(65) Prior Publication Data
US 2010/0159544 A1     Jun. 24, 2010

(30) Foreign Application Priority Data

Jul. 12, 2007    (KR) .................. 10-2007-0070219

(51) Int. Cl.
| | |
|---|---|
| C12N 1/20 | (2006.01) |
| C12N 15/00 | (2006.01) |
| C12N 15/74 | (2006.01) |
| C12P 7/46 | (2006.01) |
| C12N 9/04 | (2006.01) |
| C12N 9/12 | (2006.01) |

(52) U.S. Cl.
CPC ................ *C12P 7/46* (2013.01); *C12N 9/0006* (2013.01); *C12N 9/1217* (2013.01)
USPC ..... 435/252.3; 435/145; 435/471; 435/320.1; 536/23.2

(58) Field of Classification Search
None
See application file for complete search history.

(56) References Cited

U.S. PATENT DOCUMENTS

2007/0054387 A1 * 3/2007 Lee et al. ...................... 435/145

FOREIGN PATENT DOCUMENTS

WO    WO-2005052135    *   6/2005

OTHER PUBLICATIONS

Lee et al. Applied and Environmental Microbiology, Mar. 2006, p. 1939-1948, vol. 72, No. 3.*
Kakuda et al. Identification and Characterization of the ackA (Acetate Kinase a)-pta (Phosphotransacetylase) Operon and Complementation Analysis of Acetate Utilization by an ackA-pta Deletion Mutant of *Escherichia coli*, J Biochem (1994) 116 (4): 916-922.*
Biological Deposit Receipt, *Mannheimia* sp. 55E; KCTC 0769BP.
Biological Deposit Receipt, *Mannheimia succiniciproducens* PALK; KCTC 10973BP.
Abstract of Van der Werf MJ et al., "Environmental and physiological factors affecting the succinate product ratio during carbohydrate fermentation by *Actinobacillus* sp. 130Z", Archives of Microbiology, 1997, pp. 332-342, vol. 167, No. 6.
GenScript KI and KO Vector Construction Service, GenScript, The Biology CRO.
J. G. Zeikus et al., "Biotechnology of succinic acid production and markets for derived industrial products", Appl. Microbiol. Biotechnol., 1999, pp. 545-552, vol. 51.
Maris Laivenieks et al., "Cloning, Sequencing, and Overexpression of the *Anaerobiospirillum succiniciproducens* Phosphoenolpyruvate Carboxykinase (*pckA*) Gene", Applied and Environmental Microbiology, Jun. 1997, pp. 2273-2280, vol. 63, No. 6.
Nissim S. Samuelov et al., :Whey Fermentation by *Anaerobiospirillum succiniciproducens* for Production of a Succinate-Based Animal Feed Additive, Applied and Environmental Microbiology, May 1999, pp. 2260-2263, vol. 65, No. 5.
Pil Kim et al., "Effect of Overexpression of *Actinobacillus succinogenes* Phosphoenolpyruvate Carboxykinase on Succinate Production in *Escherichia coli*", Applied and Environmental Microbiology, Feb. 2004, pp. 1238-1241, vol. 70, No. 2.
P.C. Lee et al., "Isolation and characterization of a new succinic acid-producing bacterium, *Mannheimia succiniciproducens* MBEL55E, from bovine rumen", Appl. Microbiol. Biotechnol. 2002, pp. 663-668.
Snag Jun Lee et al., "Genome-Based Metabolic Engineering of *Mannheimia succiniciproducens* for Succinic Acid Production", Applied and Environmental Microbiology, Mar. 2006, pp. 1939-1948, vol. 72, No. 3.

* cited by examiner

*Primary Examiner* — Iqbal H Chowdhury
(74) *Attorney, Agent, or Firm* — Rabin & Berdo, P.C.

(57) ABSTRACT

The present invention relates to microbial variants producing homo-succinic acid at high yields and a method for producing homo-succinic acid using the same, more particularly, to a microbial variant constructed by disrupting a lactate dehydrogenase-encoding gene (ldhA) and an acetate kinase-encoding gene (ackA), as well as a method for producing homo-succinic acid at high concentration, which comprises culturing such variants using glucose as a carbon source in anaerobic conditions.

8 Claims, 11 Drawing Sheets

HOMO-SUCCINIC ACID PRODUCING MICROORGANISM VARIANT AND PROCESS FOR PREPARING SUCCINIC ACID USING THE SAME

CROSS-REFERENCES TO RELATED APPLICATIONS

This application is a U.S. national phase application, pursuant to 35 U.S.C. §371 of PCT/KR2008/000241, filed Jan. 15, 2008, designating the United States, which claims priority to Korean Application No. 10-2007-0070219, filed Jul. 12, 2007. The entire contents of the aforementioned patent applications are incorporated herein by this reference.

TECHNICAL FIELD

The present invention relates to microbial variants producing homo-succinic acid at high yields and a method for producing homo-succinic acid using the same, and more particularly to a microbial variant constructed by disrupting a lactate dehydrogenase-encoding gene (ldhA) and an acetate kinase-encoding gene (ackA) from succinic acid-producing microorganism, as well as a method for producing homo-succinic acid at high concentration, which comprises culturing such variants using glucose as a carbon source in anaerobic conditions.

BACKGROUND ART

Succinic acid ($HOOCCH_2CH_2COOH$), a dicarboxylic acid consisting of 4 carbons, is an organic acid having high utilities, which is widely used as a precursor of medicine, food, cosmetics, and chemical products of other industries (Zeikus et al., *Appl. Microbiol. Biotechnol.*, 51:545, 1999; Song et al., *Enzyme Microbial Technol.*, 39:352, 2006). Particularly, the demand for succinic acid is expected to be dramatically increased as a main source of biodegradable macromolecules, with the latest sharp increase in petroleum prices and increasing interest in relation to environmental pollution (Willke et al., *Appl. Microbiol. Biotechnol.*, 66:131, 2004).

Succinic acid can be produced by chemical synthesis and fermentation, and only a small amount of succinic acid for special use such as use for medicine, food additives and preservatives is produced by traditional microbial fermentation. On the contrary, most succinic acid for industrial use is currently produced through chemical synthesis methods using n-butane and acetylene derived from petroleum or liquified natural gas (LNG) by large chemical companies in America, Europe, Japan and China. Generally, the above-mentioned chemical synthesis methods have a problem of discharging large amounts of hazardous solid wastes, effluents, and waste gases (e.g., CO, etc.) generated during a process of producing succinic acid. Particularly, fossil resources having high possibility of being exhausted are used as a basic material, and thus there is an urgent need to develop a method for preparing succinic acid to replace the fossil resources with alternative ones such as renewable resources.

To overcome these problems caused by the chemical synthesis process for preparing succinic acid, studies on producing succinic acids by microbial fermentation using various renewable resources have been intensively and widely conducted by many researchers. As a result of such efforts, microorganisms, which can produce relatively large amounts of succinic acid, such as genetically engineered *Escherichia coli*, ruminal bacteria (*Actinobacillus, Bacteroides, Mannheimia, Succinimonas, Succinivibrio*, etc.) and *Anaerobiospirillum*, were identified and developed (Song et al., *Enzyme Microbial Technol.*, 39:352, 2006).

As studies for the development of novel strains producing succinic acid using microorganisms, studies using *E. coli* which can be easily manipulated and whose metabolic characteristics are relatively well studied have been actively conducted. Manipulation of *E. coli* for the production of succinic acid includes disruption of dh and pfl involved in producing lactic acid and formic acid, manipulation of ptsG, a glucose transporter gene, amplification of sfcA, a malic enzyme gene, introduction of pyc, a foreign gene derived from *Rhizobium etli* strain involved in pyruvate carboxylation, and disruption of pta, a phosphotransacetylase gene. In addition, genetically engineered *E. coli* strains, which can produce succinic acid in aerobic conditions, have been developed by manipulating genes involved in lycolysis and tricarboxylic acid(TCA) cycles and lyoxylate pathway (U.S. Pat. No. 5,770,435; Hong et al., *Biotechnol. Bioeng.*, 74:89, 2001; Venuri et al., *J. Ind. Microbiol. Biotechnol.*, 28:325, 2001; U.S. Pat. No. 6,648, 061; Lin et al., *Eng.*, 7:116, 2005; Lin et al., *Biotechnol. Bioeng.*, 90:775, 2005).

According to the studies reported to date, *Actinobacillus* and *Mannheimia* strains, which are kinds of rumen bacteria, and an obligate anaerobic bacterium, *Anaerobiospirillum* strain, are known to produce large amounts of succinic acid in anaerobic conditions as well as to have much higher productivity than genetically engineered *E. coli*.

With respect to *Actinobacillus*, Michigan Biotechnology Institute (MBI)-led team of researchers in America isolated *Actinobacillus succinogenes* 130Z strain (ATCC No. 55618) and developed a method for producing succinic acid (U.S. Pat. No. 5,504,004), and constructed various microbial variants of *A. succinogenes* using traditional chemical mutagenesis to use in developing a process for producing and purifying succinic acid (U.S. Pat. Nos. 5,521,075; 5,168,055; 5,143, 834).

However, succinic acid production processes using microbial fermentation, developed until now, have low productivit, and the yields of succinic acid per gram of carbon source are very low, thus causing difficulties in commercialization, and especially the fermentation-based succinic acid production processes incur huge costs to separate and purify succinic acid from the fermentation broth because succinic acid is produced together with large amounts of various organic acids and ethanol as byproducts during fermentation.

Particularly, *A. succinogenes* and *Anaerobiospirillum succiniciproducens* require large amounts of complex nutrients such as yeast extract during fermentation and thus incur high raw material costs for producing succinic acid, and also large amounts of $MgCO_3$ or $CaCO_3$ is added to adjust pH, which causes difficulties in separation and purification (U.S. Pat. Nos. 5,504,004 5,521,075 5,168,055; 5,143,834). To overcome the afore-mentioned shortcomings and commercialize succinic acid production using microbial fermentation, there is an urgent demand to develop a novel succinic acid-producing strain which can effectively produce homo-succinic acid at high yields but prevent byproduct formation to produce homo-succinic acid at high yields (Song et al., *Enzyme Microbial Technol.*, 39:352, 2006).

For the development of a novel succinic acid-producing strain to satisfy the above demands, the isolation of a strain having excellent succinic acid production ability, an understanding of its metabolic characteristic thereof, the completion of its genome sequence thereof, and the establishment of genetic manipulation techniques required for the construction of a genetically engineered strain should be preceded.

Although an attempt to try to produce succinic acids by amplifying a phosphoenolpyruvate carboxykinase gene (pckA) of *A. succinogenes* and *A. succiniciproducens* in *E. coli* has been reported (Kim et al., *Appl. Environ. Microbiol.*, 70:1238, 2004; Laivenieks et al., *Appl. Environ. Microbiol.*, 63:2273, 1997), there has been no report on full genome sequence of succinic acid over-producing bacteria, until now, except for *Mannheimia succiniciproduces*, and there has been no attempt to try to develop a genetically engineered succinic acid producing strain based on genome sequence, except the studies reported by the present inventors.

The present inventors have reported that they isolated *M. succiniciproducens* MBEL55E (deposited under KCTC accession no. KCTC0769BP) producing succinic acid with high efficiency from the rumen of Korean cow, completed its full genome sequence, and characterized the metabolic properties of the strain (Hong et al., *Nature Biotechnol.*, 22:1275, 2004). Also, the present inventors have constructed a bacterial mutant *M. succiniciproducens* LPK (deposited under KCTC accession no. KCTC10558BP) by disrupting a gene encoding lactate dehydrogenase (ldhA) and a gene encoding pyruvate formate-lyase (pfl) in *M. succiniciproducens* MBEL55E. In addition, the present inventors have constructed a microbial variant (*M. succinciproducens* LPK7 (deposited under KCTC accession no. KCTC1062BP)) by disrupting a phosphotransacetylase gene (pta) and an acetate kinase gene (ackA) in said microbial variant, *M. succiniciproducens* LPK, thus increasing the production of succinic acid (WO 2005/052135 A1). However, in case of such microbial variants, although the formation of byproducts, lactic acid, formic acid and acetic acid could be suppressed effectively, large amounts of pyruvic acid accumulated as a byproduct during fermentation. Most of all, the growth rate of *M. succiniciproducens* LPK7 has become so low compared with the wild-type strain that an excellent succinic acid productivity could not be achieved. Although the present inventors have constructed a microbial variant (*M. succinciproducens* PALK, deposited under KCTC accession no. KCTC10973BP) by disrupting a lactate dehydrogenase-encoding gene (ldhA), a phosphotranacetylase-encoding gene (pta), and an acetate kinase-encoding gene (ackA) in *M. succinciproducens* MBEL55E (PCT/KR2007/003574), and as a result, achieved an increase in cell growth rate and improvement of succinic acid productivity, there is still a need for development of a better succinic acid producing microbial variant.

The present inventors have made extensive efforts to construct a microbial variant (*M. succiniciproducens* ALK), by disrupting a lactate dehydrogenase gene (ldhA) and an acetate kinase gene (ackA) in *M. succiniciproducens* MBEL55E. Variant ALK has been deposited in compliance with the Budapest Treaty on Nov. 29, 2012 at the Korean Collection for Type Cultures located at Korea Research Institute of Bioscience and Biotechnology, 125 Gwahak-ro, Yuseong-gu, Daejeon 305-806, Republic of Korea under deposit accession no. KCTC 12326BP. The deposit will be maintained for at least thirty (30) years and will be irrevocably and without restriction released to the public upon the grant of a patent. The availability of a deposit does not constitute a license to practice the subject invention in derogation of patent rights granted by government action. The present inventors have also constructed a variant (*M. succincipro-ducens* ALKt) as a variant having the same effect as that of said ALK variant based on the result of a virtual cell model, and found that when the microbial variants were cultured using glucose as a carbon source in anaerobic conditions, they can produce homo-succinic acid at high yields, thereby completing the present invention.

SUMMARY OF THE INVENTION

Therefore, it is an object of the present invention to provide a rumen microbial variant lacking a lactate dehydrogenase gene (ldhA) and an acetate kinase gene (ackA), which has high succinic acid productivity, and a method for preparing the microbial variant.

Another object of the present invention is to provide a method for producing homo-succinic acid at high yields without the accumulation of other byproducts by culturing the microbial variant using glucose as a carbon source in anaerobic conditions.

To achieve the above objects, the present invention provides a succinic acid-producing microbial variant lacking a lactate dehydrogenase gene (ldhA) and an acetate kinase gene (ackA) while maintaining a phosphotransacetylase gene (pta) in the succinic acid producing microorganisms, which can produce succinic acid at high concentration in anaerobic conditions.

The present invention also provides a succinic acid-producing microbial variant *M. succiniciproducens* ALKt, in which a gene encoding phosphotransacetylase (pta) is introduced into *M. succiniciproducens* PALK lacking a lactate dehydrogenase gene (ldhA), a phosphotransacetylase gene (pta) and an acetate kinase gene (ackA).

The present invention also provides a succinic acid-producing microbial variant *M. succiniciproducens* ALK, in which a lactate dehydrogenase gene (ldhA) and an acetate kinase gene (ackA) are disrupted in *M. succiniciproducens* MBEL55E.

Additionally, the present invention provides a method for producing a succinic acid-producing microbial variant, which comprises the steps of: (a) obtaining a succinic acid-producing microbial variant lacking a gene encoding lactate dehydrogenase (ldhA) by disrupting a gene encoding lactate dehydrogenase (ldhA) in the genome of a succinic acid-producing microorganism by homologous recombination; and (b) obtaining a succinic acid-producing microbial variant lacking a gene encoding lactate dehydrogenase (ldhA) and a gene encoding acetate kinase (ackA) by disrupting a gene encoding acetate kinase (ackA) in the genome of the succinic acid-producing microbial variant lacking a gene encoding lactate dehydrogenase (ldhA) by homologous recombination Further the present invention provides a method for preparing a succinic acid-producing microbial variant, in which a gene encoding phosphotransacetylase (pta) is introduced into a succinic acid-producing microbial variant lacking a lactate dehydrogenase gene (ldhA), a phosphotransacetylase gene (pta) and an acetate kinase gene (ackA).

Furthermore, the present invention provides a method for producing succinic acid, which comprises the steps of culturing the succinic acid-producing microbial variant in anaerobic conditions, and recovering succinic acid from the culture broth.

Another features and embodiments of the present invention will be more clarified from the following detailed descriptions and the appended claims.

DETAILED DESCRIPTION OF THE INVENTION, AND PREFERRED EMBODIMENTS

Figure 1:
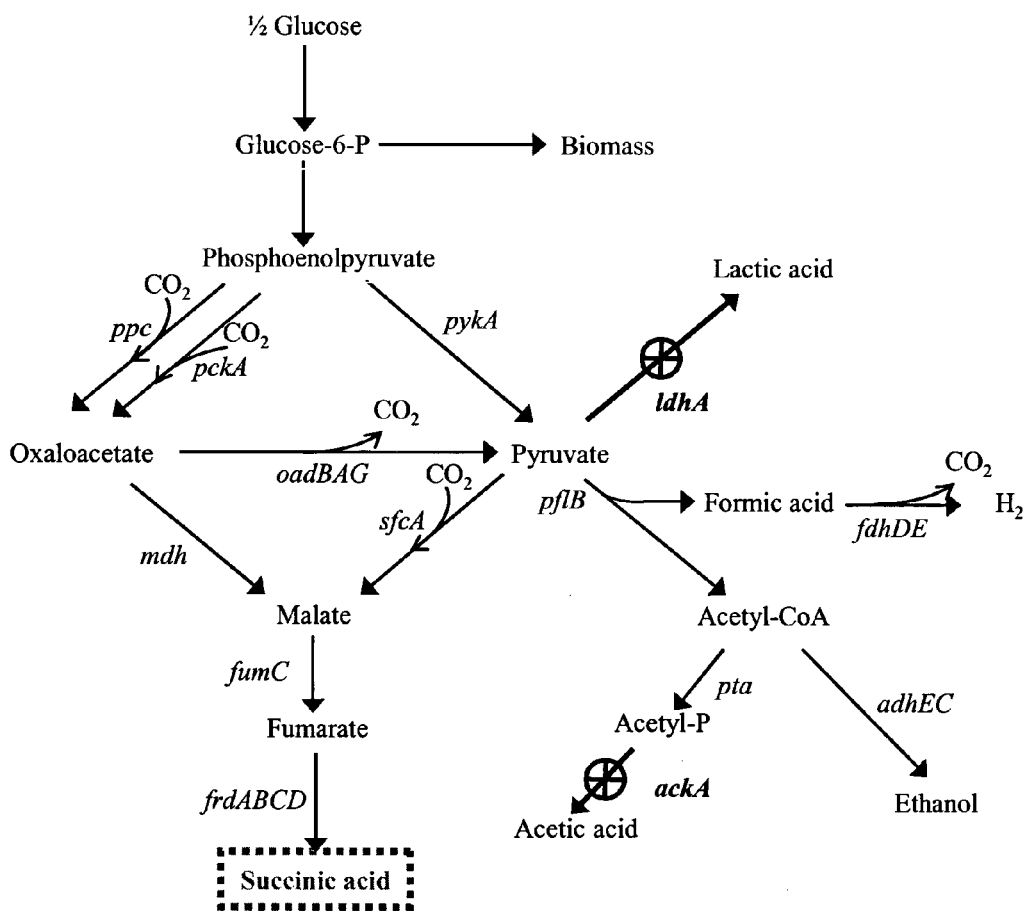
FIG. 1 is a schematic diagram showing the homo-succinic acid production pathway in the *Mannheimia* microbial variant, in which homo-succinic acid is produced at high yields.

In the present invention, a virtual cell model was designed for developing a microbial variant to effectively produce homo-succinic acid at high concentration by minimizing formation of byproducts. The genome of *M. succiniciproducens* MBEL55E consists of 2,314,078 base pairs (Hong et al., *Nat. Biotechnol.*, 22:12275, 2005) and contains 2,384 candidate genes, which was revealed by bioinformatics (Kim et al., *Biotechnol, Bioeng.*, 97:657, 2007). The genes of *M. succiniciproducens* MBEL55E are distributed within the whole genome, and categorized by cellular functions, with which the characteristics of whole genome were evaluated. The overall analysis of the genomic information is provided to configure a virtual cell model of *M. succiniciproducens* MBEL55E. The virtual cell comprises 686 enzyme reactions and 516 metabolites, with which the change of metabolic cascades was quantitatively compared.

An enormous number of microbial variants are needed to construct multi-gene mutants using the combination of each gene. In reality, because constructing such huge number of microbial variants on the lab bench is as difficult as impossible, in silico simulation was performed using a virtual cell model (KR patent No.630,836). Particularly, after each of two or three genes was combined and eliminated in silico, the rate of product formation and specific growth rate for each variant were calculated, from which a trade off curve was deduced. Additionally, on said trade off curve, the combination of genes to be eliminated was chosen, which could postulate the eliminating combination of genes for minimizing the suppression of cell growth rate and maximizing the production rate of succinic acid. In the present invention, a ΔackAΔldhA strain, the combination having ackA and ldhA disrupted simultaneously, turned out to produce an optimal curve for succinic acid the production rate versus the specific growth rate of the strain.

In the present invention, it was examined whether a succinic acid-producing microbial variant, which contains a gene encoding phosphotransacetylase (pta) and has a gene encoding lactate dehydrogenase (ldhA) and a gene encoding acetate kinase (ackA) disrupted, could produce succinic acid at high concentration in anaerobic conditions.

To examine the ability thereof, a gene encoding phosphotransacetylase (pta) was reexpressed in *M. succiniciproducens* PALK constructed by disrupting a lactate dehydrogenase gene (ldhA), a phosphotransacetylase gene (pta) and an acetate kinase gene (ackA) from *M. succiniciproducens* MBEL55E, a kind of succinic acid-producing bacteria, thus constructing a microbial variant (M succiniciproducens ALKt).

In addition, a microbial variant (*M. succiniciproducens* ALK) was constructed by disrupting a lactate dehydrogenase gene (ldhA) and an acetate kinase gene (ackA) in *M. succiniciproducens* MBEL55E, a kind of succinic acid-producing bacteria.

Therefore, in one aspect, the present invention relates to a succinic acid-producing microbial variant lacking a lactate dehydrogenase-encoding gene (ldhA) and an acetate kinase-encoding gene (ackA) while maintaining a phosphotransacetylase gene (pta) in a succinic acid-producing microorganism, which is capable of producing homo-succinic acid at high concentration in anaerobic conditions.

In the present invention, said succinic acid-producing microorganisms are preferably selected from the group consisting of *Actinobacillus* sp., *Anaerobiospirillum* sp., *Bacteroides* sp., *Mannheimia* sp., *Succinimonas* sp., *Succinivibrio* sp., and genetically engineered *E. coli*, more preferably *Mannheimia* sp., but not limited thereto, and any microorganisms can be used without limitations as long as it can produce succinic acid under anaerobic conditions.

In the present invention, said succinic acid-producing microbial variant can be constructed by disrupting a lactate dehydrogenase-encoding gene (ldhA) and an acetate kinase gene (ackA), if a succinic acid-producing microorganism contains a phosphotransacetylase gene (pta). And said succinic acid-producing microbial variant can be constructed by disrupting a lactate dehydrogenase-encoding gene (ldhA) and an acetate kinase gene (ackA), and introducing a phosphotransacetylase gene (pta), if a succinic acid-producing microorganism has intrinsically or extrinsically lost a phosphotransacetylase gene (pta).

The present invention also relates to a succinic acid-producing microbial variant (*M. succiniciproducens* ALKt), in which a phosphotransacetylase gene (pta) is introduced into a succinic acid-producing microbial variant (*M. succiniciproducens* PALK) lacking a lactate dehydrogenase gene (ldhA), a phosphotransacetylase gene (pta) and an acetate kinase gene (ackA).

The present invention also relates to a succinic acid-producing microbial variant (*M. succiniciproducens* ALK), in which an acetate kinase gene (ackA) is disrupted in a succinic acid-producing microbial variant (*M. succiniciproducens* MFLK) constructed by disrupting a lactate dehydrogenase gene (ldhA) from *M. succiniciproducens* MBEL55E.

In the present invention, said succinic acid-producing microbial variants are preferably homo-fermentative microorganisms capable of producing only succinic acid at high concentration while producing little or no other organic acids and ethanol as byproducts.

Said succinic acid-producing microbial variants can produce homo-succinic acid at high concentration, because formation of byproducts such as ethanol and other organic acids, during general fermentation process can be effectively prevented when glucose is used as a carbon source in anaerobic conditions.

From partial genetic information (16s rRNA), metabolic features, and fermentation results of succinic acid-producing microorganisms such as *A. succinogenes, A. succiniciproducens* and various succinic acid-producing microorganisms known to produce succinic acid, it was found that main biosynthesis pathways for succinic acid production from a carbon source in said succinic acid-producing microorganisms are almost identical with biosynthesis pathway for succinic acid production in *Mannheimia* sp. (Van der Werf et al., *Arch Microbiol.*, 167:332, 1997; Laivenieks et al., *Appl. Environ. Microbiol.*, 63:2273, 1997; Samuelov et al., *App. Environ. Microbiol.*, 65:2260, 1999; Kim et al., *Appl. Environ. Microbiol.*, 70:1238, 2004). Especially, all bacteria, which are involved in the production of succinic acid, convert phosphoenolpyruvate and pyruvate, C3 compounds into oxaloacetate and malate, C4 compounds, using $CO_2$-fixing enzymes upon succinic acid production, thus producing succinic acid (FIG. 1). In addition, the succinic acid-producing microorganisms produce acetic acid, formic acid, lactic acid and ethanol as fermentation byproducts in anaerobic conditions.

In another aspect, the present invention relates to a method for producing a succinic acid-producing microbial variant comprising the steps of: (a) obtaining a succinic acid-producing microbial variant lacking a gene encoding lactate dehydrogenase (ldhA) by disrupting a gene encoding lactate dehydrogenase (ldhA) in the genome of a succinic acid-producing microorganism by homologous recombination; and (b) obtaining a succinic acid-producing microbial variant lacking a gene encoding lactate dehydrogenase (ldhA) and a gene encoding acetate kinase (ackA) by disrupting a gene encoding acetate kinase (ackA) in the genome of the succinic acid-producing microbial variant lacking a gene encoding lactate dehydrogenase (ldhA) by homologous recombination.

In the present invention, homologous recombination is preferably performed by using a genetic exchange vector containing a disrupted ldhA and a genetic exchange vector containing a disrupted ackA.

In the present invention, said genetic exchange vector containing a disrupted ldhA is preferably pMLKO-sacB and pMF1 dhA, and said genetic exchange vector containing a disrupted ackA is preferably pPTA-sacB and pAckAKO.

In still another aspect, the present invention relates to method for constructing a succinic acid-producing microbial variant, which comprises introducing a phosphotransacetylase gene (pta) into a succinic acid-producing microbial variant lacking a gene encoding lactate dehydrogenase (ldhA), a gene encoding acetate kinase (ackA) and a phosphotransacetylase gene (pta).

In the present invention, said succinic acid-producing microbial variant lacking a lactate dehydrogenase gene (ldhA) and an acetate kinase gene (ackA) and a phosphotransacetylase gene (pta) is preferably *M. succiniciproducens* PALK (KCTC10973BP).

In yet another aspect, the present invention relates to a method for producing succinic acid, which comprises the steps of: culturing said succinic acid-producing microbial variants in anaerobic conditions; and recovering succinic acid from the culture broth In the present invention, glucose is preferably used as a carbon source for the culture.

In the present invention, the culture of genetically engineered microorganisms and the production process of succinic acid can be carried out by culture methods known in the conventional fermentation process, and methods for separating and purifying succinic acid.

EXAMPLES

The present invention will hereinafter be described in further details by examples. It will however be obvious to a person skilled in the art that these examples are given for illustrative purpose only, and the present invention is not limited to or by the examples.

Particularly, the following examples illustrate only specific vectors and *Mannheimia* sp., which is a succinic acid-producing microorganism, as a host cell in order to delete the genes according to the present invention. However, it is obvious to a person skilled in the art that a microbial variant producing homo-succinic acid can be obtained even when other kinds of vectors and succinic acid producing microorganisms are used.

It is also obvious to one skilled in the art that the effect of a microbial variant lacking a lactate dehydrogenase gene (ldhA) and an acetate kinase gene (ackA) is the same as that of a microbial variant constructed by reexpressing a phosphotransacetylase gene (pta) in a microbial variant lacking a lactate dehydrogenase gene (ldhA), an acetate kinase gene (ackA) and a phosphotransacetylase gene (pta).

Example 1

Construction of ldhA Disruption Vector (pMLKO-sacB)

In order to disrupt a lactate dehydrogenase gene (ldhA) in the genome of a succinic acid producing microorganism by homologous recombination, a genetic exchange vector was constructed in the following manner. First, the genomic DNA of *M. succiniciproducens* MBEL55E (KCTC 0769BP), as a template, was subjected to PCR using primers set forth in SEQ ID NO: 1 and SEQ ID NO: 2 below, and then, the obtained PCR fragment was cut with SacI and PstI and introduced into pUC18 vector (New England Biolabs, Inc., USA), thereby constructing pUC18-L1.

SEQ ID NO: 1: 5'-CAGTGAAGGAGCTCCGTAACGCATCCGCCG-3'

SEQ ID NO: 2: 5'-CTTTATCGAATCTGCAGGCGGTTTCCAAAA-3'

In addition, the genomic DNA of *M. succiniciproducens* MBEL55E, as a template, was subjected to PCR using primers set forth in SEQ ID NO: 3 and SEQ ID NO: 4 below, and then the obtained PCR fragment was cut with PstI and HindIII, and introduced into the pUC18-L1, thereby constructing pUC18-L1-L2.

SEQ ID NO: 3: 5'-GTACTGTAAACTGCAGCTTTCATAGTTAGC-3'

SEQ ID NO: 4: 5'-GCCGAAAGTCAAGCTTGCCGTCGTTTAGTG-3'

In order to insert a kanamycin-resistant gene as a selection marker in the pUC18-L1-L2, pUC4K vector (Pharmacia, Freiburg, Germany) was cut with PstI, and the kanamycin-resistant gene was fused with pUC18-L1-L2 cut with PstI, thereby constructing pUC18-L1-KmR-L2. A linker set forth in SEQ ID NO: 5 was inserted into pUC18-L1-KmR-L2 cut with SacI, thereby making a new XbaI cutting site.

Figure 2:
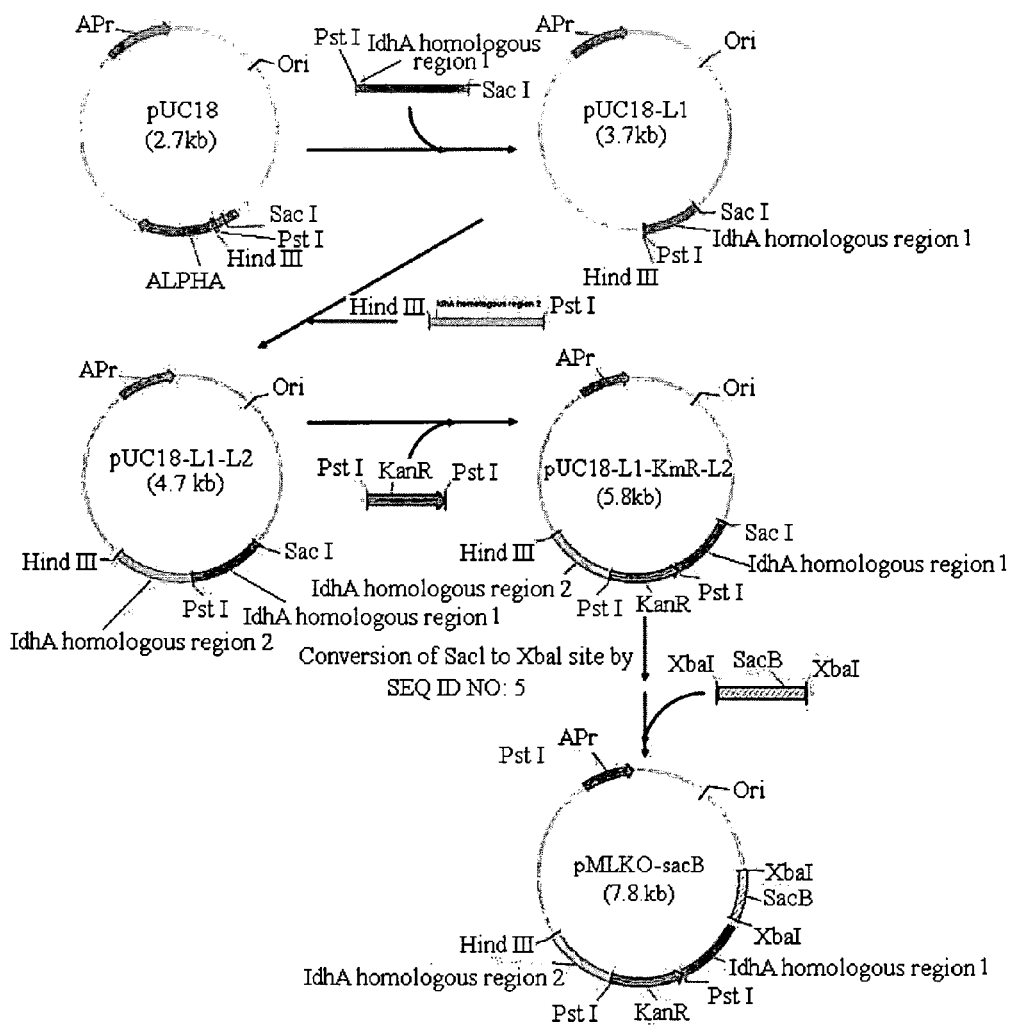
FIG. 2 shows a process of constructing a vector for disrupting ldhA (pMLKO-sacB).

SEQ ID NO: 5: 5'-TCTAGAAGCT pKmobsacB (Schafer et al., *Gene*, 145:69, 1994), as a template, was subjected to PCR using primers set forth in SEQ ID NO: 6 and SEQ ID NO: 7 below. Then the resulting PCR fragment was cut with XbaI, and inserted into the new XbaI restriction enzyme site, thereby constructing pMLKO-sacB (FIG. 2).

SEQ ID NO: 6: 5'-GCTCTAGACCTTCTATCGCCTTCTTGACG-3'

SEQ ID NO: 7: 5'-GCTCTAGAGGCTACAAAATCACGGGCGTC-3'

Example 2

Construction of ldhA Disruption Vector (pMFldhA)

In order to disrupt a lactate dehydrogenase gene (ldhA) in the genome of *M. succiniciproducens* MBEL55E by homologous recombination, a genetic exchange vector was constructed in the following manner. First, the genomic DNA of *M. succiniciproducens* MBEL55E, as a template, was subjected to PCR using primers set forth in SEQ ID NO: 8 and SEQ ID NO: 9 below, and then the obtained PCR fragment was cut with BamHI and PstI and introduced into pSacHRO6 (Park et al., PNAS., 104:7797, 2007), thereby constructing pldhAL.

SEQ ID NO: 8: 5'-TTGCAACATGGCGAACTTAGC-3'

SEQ ID NO: 9: 5'-ATATCTGCAGTTAATAAAATGCGCGACGG-3'

Next, the genomic DNA of *M. succiniciproducens* MBEL55E, as a template, was subjected to PCR using primers set forth in SEQ ID NO: 10 and SEQ ID NO: 11 below, and then, the obtained PCR fragment was cut with SalI and SphI, and introduced into the pldhAL, thereby constructing pldhALR.

SEQ ID NO: 10:
5' 5'-ATATGTCGACCAACTTTCATAGTTAGCTCC-3'

Figure 3:
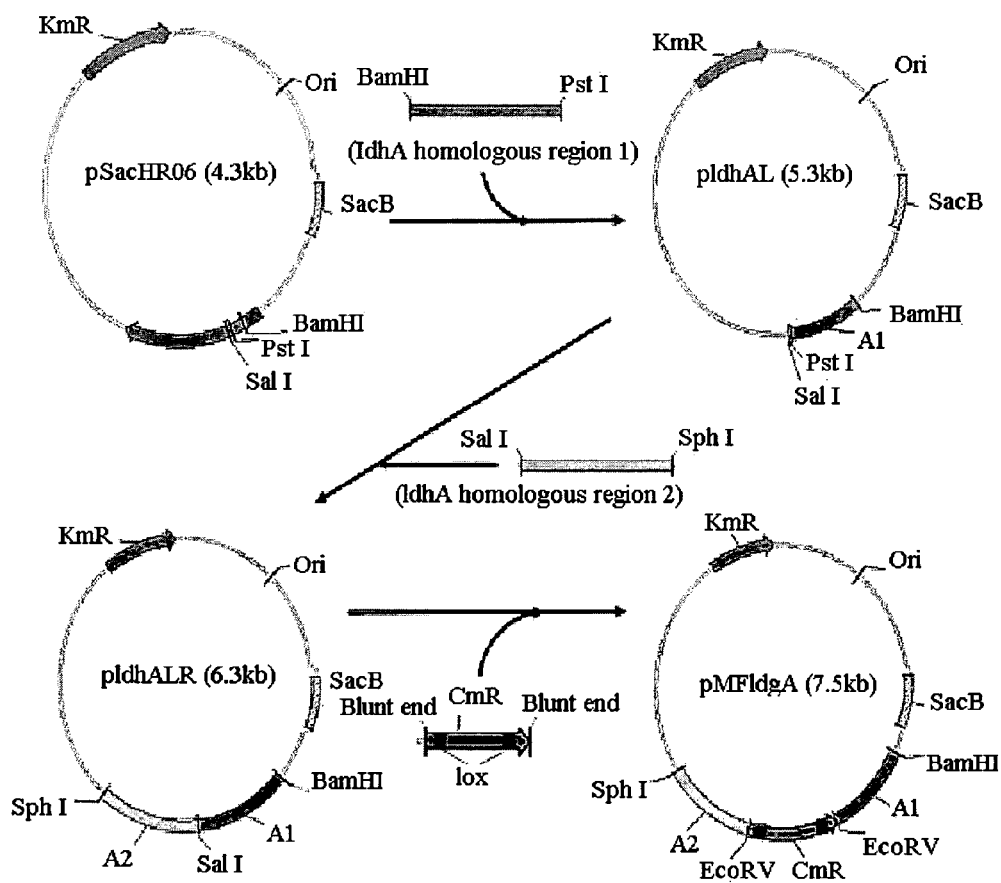
FIG. 3 shows a process of constructing a vector for disrupting ldhA (pMFldhA).

SEQ ID NO: 11:
5'-ATCCGCATGCTTGCCGTCGTTTAGTGCTG-3' pMSmulox (Kim et al., *FEMS Microbial Lett.*, 278:78, 2008), as a template, was subjected to PCR using primers set forth in SEQ ID NO: 12 and SEQ ID NO: 13 below. Then the resulting PCR fragment was treated with S1 nuclease to generate blunt ends, and inserted into pldhALR, thereby constructing pMFldhA (FIG. 3).

SEQ ID NO: 12:
5'-ATATAAGCTTTACCGTTCGTATAGCATACATTATACGAAGTTATGAC

GGGCTGGCGGTATTGG-3'

SEQ ID NO: 13:
5'-AATTCCCGGGTACCGTTCGTATAATGTATGCTATACGAA GTTATTG

CCAGTTGATCACCTCGGG-3'

Example 3

Construction of *M. succiniciproducens* LK Strain

Figure 4:
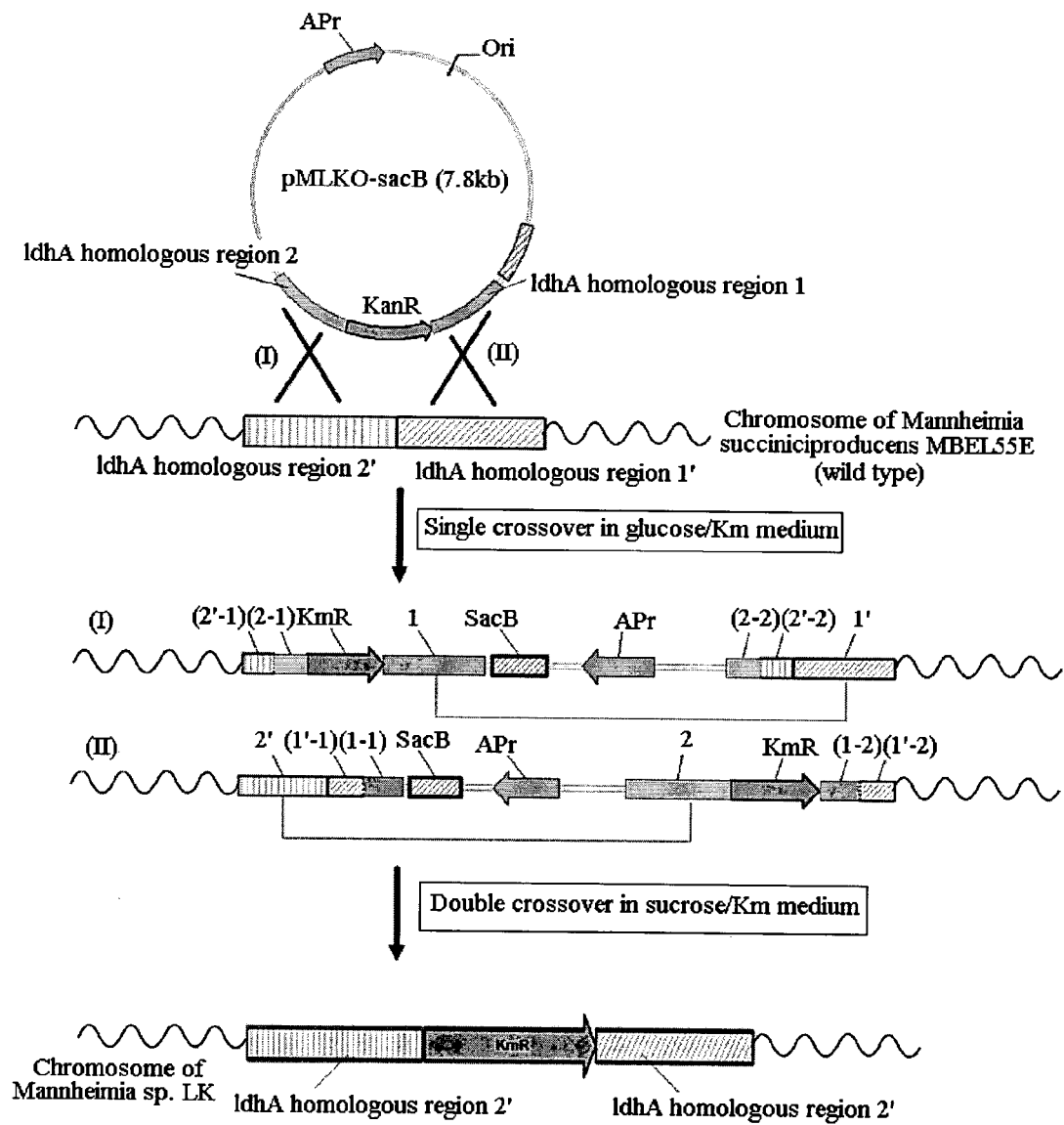
FIG. 4 shows a process of constructing a microbial variant (*M. succinicproducens* LK) by disrupting ldhA in *M. succiniciproducens* MBEL55E.

A microbial variant (*M. succiniciproducens* LK) was constructed by disrupting ldhA gene in the genome of *M. succiniciproducens* MBEL55E (FIG. 4).

Specifically, *M. succiniciproducens* MBEL55E (KCTC 0769BP) was plated on LB-glucose agar medium containing 10 g/L of glucose, and cultured at 37° C. for 36 hours. The colony formed was inoculated in 10 ml of LB-glucose liquid medium, and cultured for 12 hours. 1% of the culture broth, which had been sufficiently grown, was inoculated in 100 ml of LB-glucose liquid medium, and cultured in a shaking incubator at 200 rpm and 37° C.

When culture broth reached an $OD_{600}$ of about 0.3-0.4 after 4~5 hours, it was centrifuged at 4° C. and 4,500 rpm for 20 minutes to collect cells. Then, the cells were resuspended in 200 ml of 10% glycerol solution at 4° C. and centrifuged at 4° C. and 5,500 rpm for 20 minutes to collect cells. After resuspending and collecting in one-half of the above glycerol solution twice in the same manner as the above-described processes, the cells were suspended in glycerol solution at a volume ratio of 1:1, to obtain cell concentrate.

The cell concentrate thus obtained was mixed with the genetic exchange vector pMLKO-sacB constructed in Example 1, and then pMLKO-sacB was introduced into the cultured *M. succiniciproducens* MBEL55E by electroporation under conditions of 1.8 kV, 25 μF and 200 ohms. 1 ml of LB-glucose liquid medium was added to the pMLKO-sacB-introduced strain, and precultured in a shaking incubator at 37° C. and 200 rpm for one hour. The culture broth was plated on LB-glucose solid medium containing an antibiotic kanamycin (final concentration of 25 μg/ml) and cultured at 37° C. for 48 hours or more. In order to select colonies where only double crossover occurred, the colonies formed were streaked on LB-sucrose solid medium containing kanamycin (25 μg/ml) and 100 g/L sucrose. After 24 hours, the formed colonies were streaked again on the same medium.

The colonies (variant) formed on the medium were cultured in LB-glucose liquid medium containing an antibiotic, and genomic DNA was isolated from the cultured strain by the method described in Rochelle et al. (Rochelle et al., *FEMS Microbiol. Lett.*, 100:59, 1992). Using the isolated mutant genomic DNA as a template, PCR was performed, and the PCR product was electrophoresed to confirm the disruption of ldhA gene in the genomic DNA.

In order to confirm the disruption of the ldhA gene, PCRs were performed twice in the following manners. First, the mutant genomic DNA, as a template, was subjected to PCR using primers set forth in SEQ ID NO: 14 and SEQ ID NO: 15.

SEQ ID NO: 14: 5'-GACGTTTCCCGTTGAATATGGC-3' (KM1)

SEQ ID NO: 15: 5'-CATTGAGGCGTATTATCAGGAAAC-3' (LU1)

Then, the mutant genomic DNA, as a template, was subjected to PCR using primers set forth in SEQ ID NO: 16 and SEQ ID NO: 17. The PCR fragments obtained in the two PCRs were subjected to gel electrophosis to confirm the disruption of ldhA by their size (1.5 kb).

SEQ ID NO: 16: 5'-GCAGTTTCATTTGATGCTCGATG (KM2)

SEQ ID NO: 17: 5'-CCTCTTACGATGACGCATCTTTCC (LU2)

The PCR fragments of the genomic DNA having disrupted ldhA were confirmed by the fact that the product resulted from the PCR using the primers of SEQ ID NO: 14 (KM1) and SEQ ID NO: 15 (LU1) has a size of 1.5 kb, and at the same time, the product resulted from the PCR using the primers of SEQ ID NO: 16 (KM2) and SEQ ID NO: 17 (LU2) has a size of 1.7 kb. The position of each primer is shown in FIG. 4.

Example 4

Construction of *M. succiniciproducens* MFLK Strain

Figure 5:
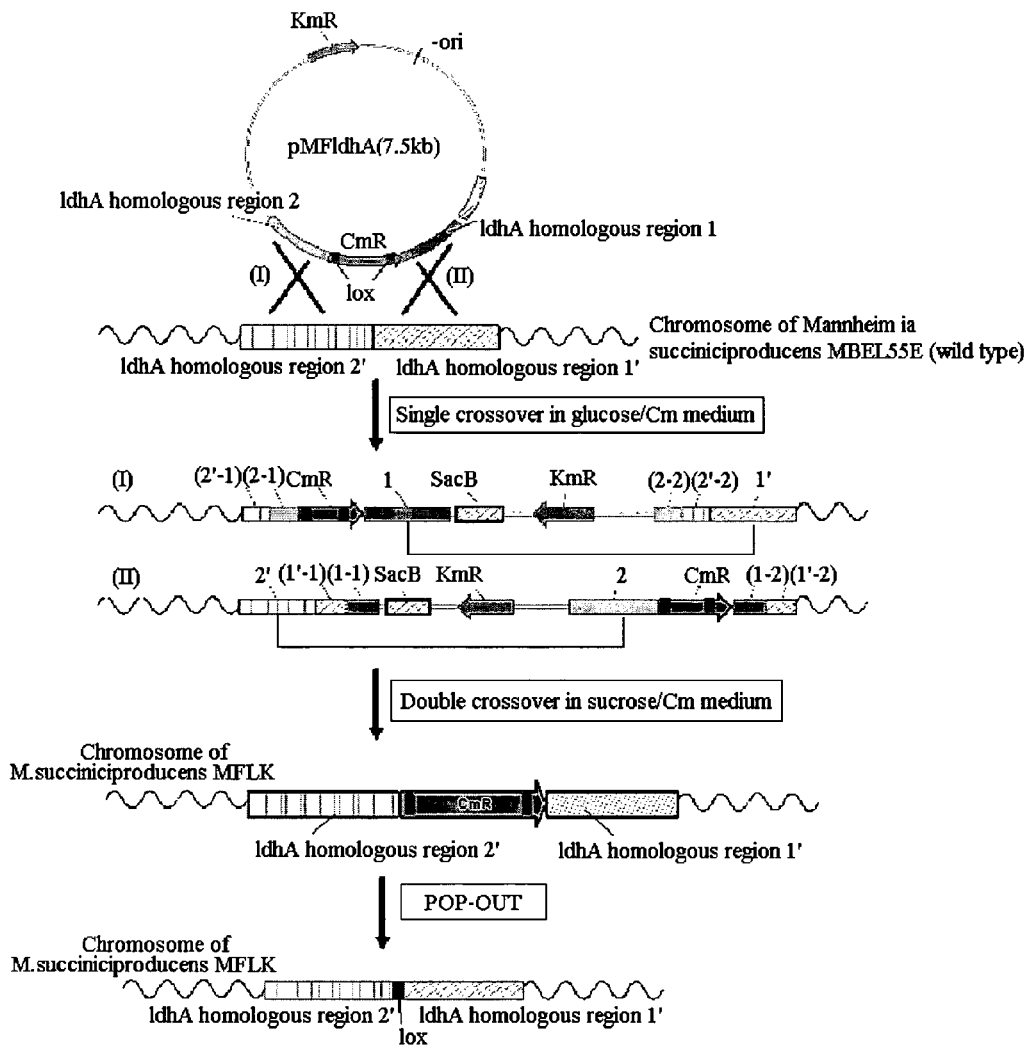
FIG. 5 shows a process of constructing a microbial variant (M succinicproducens MFLK) by disrupting ldhA from *M. succiniciproducens* MBEL55E.

A microbial variant (*M. succiniciproducens* MFLK) was constructed by disrupting ldhA gene in the genome of *M. succiniciproducens* MBEL55E (FIG. 5).

Specifically, *M. succiniciproducens* MBEL55E (KCTC0769BP) was plated on TSA-glucose agar medium containing 10 g/L of glucose, and cultured at 37° C. for 36 hours. The colony formed was inoculated in 10 ml of LB-glucose liquid medium, and cultured for 12 hours. 1% of the culture broth, which had been sufficiently grown, was inoculated in 100 ml of LB-glucose liquid medium, and cultured in a shaking incubator at 200 rpm and 37° C.

The cell concentrate obtained from said culture broth in the same manner as described in Example 3 was mixed with the genetic exchange vector pMFldhA constructed in Example 2, and then pMFldhA was introduced into the cultured *M. succiniciproducens* MBEL55E by electroporation under conditions of 1.8 kV, 25 µF and 200 ohms. 1 ml of LB-glucose liquid medium was added to the pMFldhA-introduced strain, and precultured in a shaking incubator at 37° C. and 200 rpm for one hour. The culture broth was plated on TSA-glucose agar medium containing an antibiotic chloramphenicol (final concentration of 6.8 µg/ml) and cultured at 37° C. for 48 hours or more. In order to select colonies where only double crossover occurred, the colonies formed were streaked on TSA-sucrose plate containing chloramphenicol (final concentration of 6.8 µg/ml) and 100 g/L sucrose. After 24 hours, the formed colonies were streaked again on the same medium. Using the colonies obtained by repeating the above process, PCR was performed, and the resulting PCR product was electrophoresed to confirm the disruption of ldhA gene in the genomic DNA.

In order to confirm the disruption of the ldhA gene, PCRs were performed twice in the following manners. First, the mutant genomic DNA, as a template, was subjected to PCR using primers set forth in SEQ ID NO: 18 and SEQ ID NO: 19.

SEQ ID NO: 18:
5'-ACCTTTACTACCGCACTGCTGG-3'

SEQ ID NO: 19:
5'-GCGGGAGTCAGTGAACAGGTAC-3'

Then, the mutant genomic DNA, as a template, was subjected to PCR using primers set forth in SEQ ID NO: 20 and SEQ ID NO: 21. The PCR fragments obtained in the PCRs were subjected to gel electrophoresis to confirm the disruption of ldhA gene in the genomic DNA.

SEQ ID NO: 20:
5'-TTACAGCTCACCGAAAGCACGC-3'

SEQ ID NO: 21:
5'-ATAAGCGGCGTTAACCTTCAAC-3'

In order to disrupt the antibiotic gene from said ldhA double-crossover microbial variant, cell concentrate of the ldhA double-crossover variant was obtained, and then transformed with TS plasmid pCRX5 (Kim et al., *FEMS Microbial Lett.*, 278:78, 2008) in the same manner as described above. pCRX5 inserted into cells expresses Cre recombinase to disrupt chloramphenicol gene located between lox sites. An ldhA double-crossover microbial variant containing pCRX5 was inoculated in TSB liquid medium containing ampicillin and cultured for 24 hours, and then plated on TSB agar medium containing ampicillin. The ldhA double-crossover microbial microbial variant lacking an antibiotic gene was confirmed by PCR using primers set forth in SEQ ID NO: 22 and SEQ ID NO:23.

SEQ ID NO: 22:
5'-TTACAGCTCACCGAAAGCACGC-3'

SEQ ID NO: 23:
5'-AATTCGTAACGCATCCGCCG-3'

Then, in order to disrupt pCRX5, cells (ldhA double mutant strain) was transferred to TSB liquid medium containing no antibiotic, cultured at 42° C. for 24 hours, and cultured again on TSB agar medium containing no antibiotic (30° C.).

The formed colony was streaked on TSB medium containing ampicillin and antibiotic-free TSB medium and cultured at 30° C., thus obtaining pCRX5-disrupted *M. succinicproducens* MFLK that can not grow on an ampicillin-containing medium.

Example 5

Construction of Genetic Exchange Vector (pPTA-sacB) for the Disruption of pta and ackA In order to disrupt a phosphotransacetylase gene (pta) and an acetate kinase gene (ackA) in the genome of *M. succiniciproducens* LK strain by homologous recombination, a genetic exchange vector was constructed in the following manner. A vector pKmobsacB containing a sacB gene (GenBank 02730), as a template, was subjected to PCR using primers set forth in SEQ ID NO: 24 and SEQ ID NO: 25. The resulting sacB product was cut with PstI and BamHI and inserted into pUC19 (Stratagene Cloning Systems. USA), thereby constructing pUC19-sacB.

SEQ ID NO: 24:
5'-AGCGGATCCCCTTCTATCGCCTTCTTGACG-3'

SEQ ID NO: 25:
5'-GTCCTGCAGGGCTACAAAATCACGGGCGTC-3'

Meanwhile, the genomic DNA of *M. succiniciproducens* LK (KCTC10558BP), as a template, was subjected to PCR using primers set forth in SEQ ID NO: 26 and SEQ ID NO: 27, and the resulting PCR fragment was cut with XbaI and BamHI and inserted into pUC19, thereby constructing pUC19-PTA 1.

SEQ ID NO: 26:
5'-GCTCTAGATATCCGCAGTATCACTTTCTGCGC-3'

SEQ ID NO: 27:
5'-TCCGCAGTCGGATCCGGGTTAACCGCACAG-3'

Then, the genomic DNA of *M. succiniciproducens* LK, as a template, was subjected to PCR using primers set forth in SEQ ID NO: 28 and SEQ ID NO: 29, and the resulting PCR fragment was cut with XbaI and SacI, and inserted into the pUC19-PTA 1, thereby constructing pUC19-PTA 12.

SEQ ID NO: 28:
5'-GGGGAGCTCGCTAACTTAGCTTCTAAAGGCCATGTTT CC-3'

SEQ ID NO: 29:
5'-GCTCTAGATATCCGGGTCAATATCGCCGCAAC-3'

Figure 6:
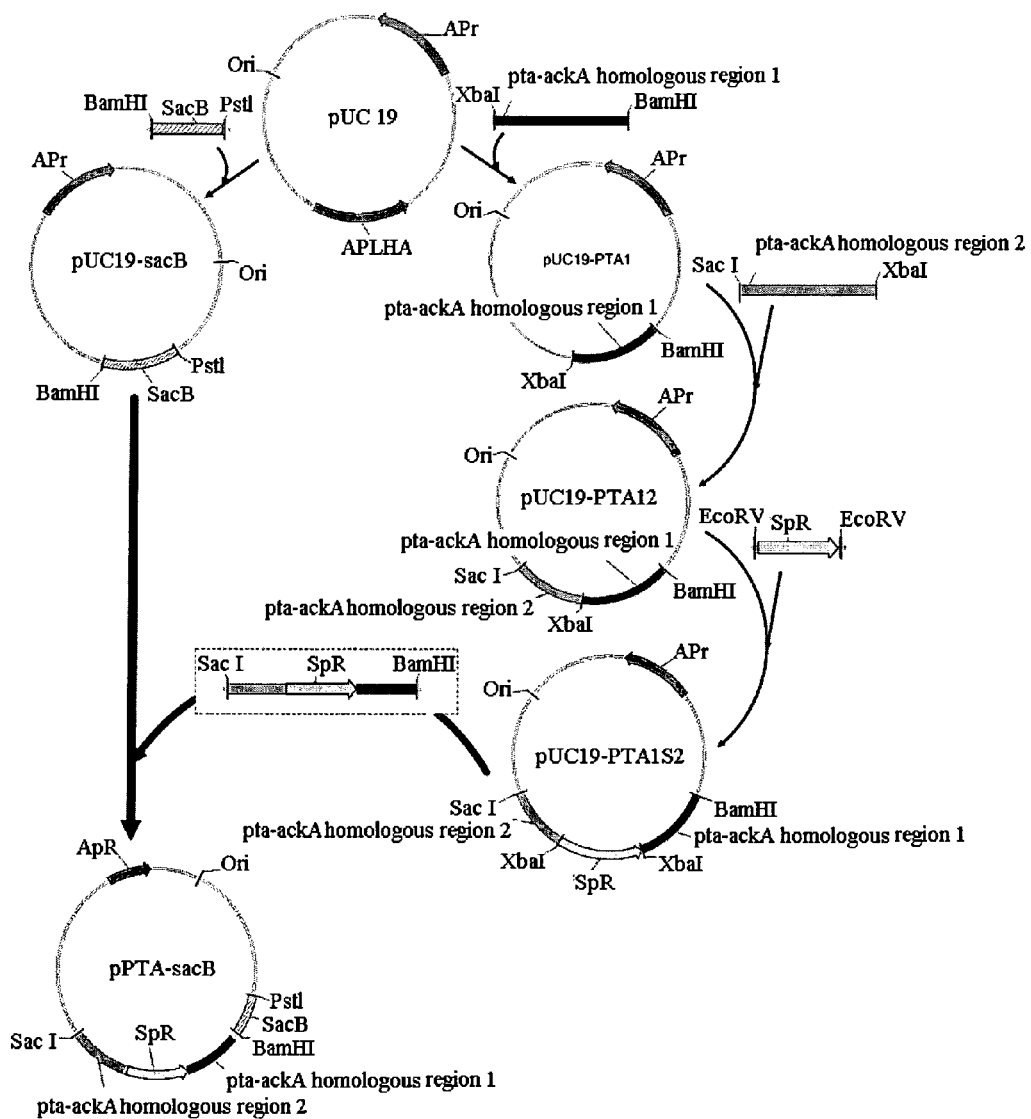
FIG. 6 shows a process of constructing a vector for disrupting pta and ackA (pPTA-sacB).
Figure 7:
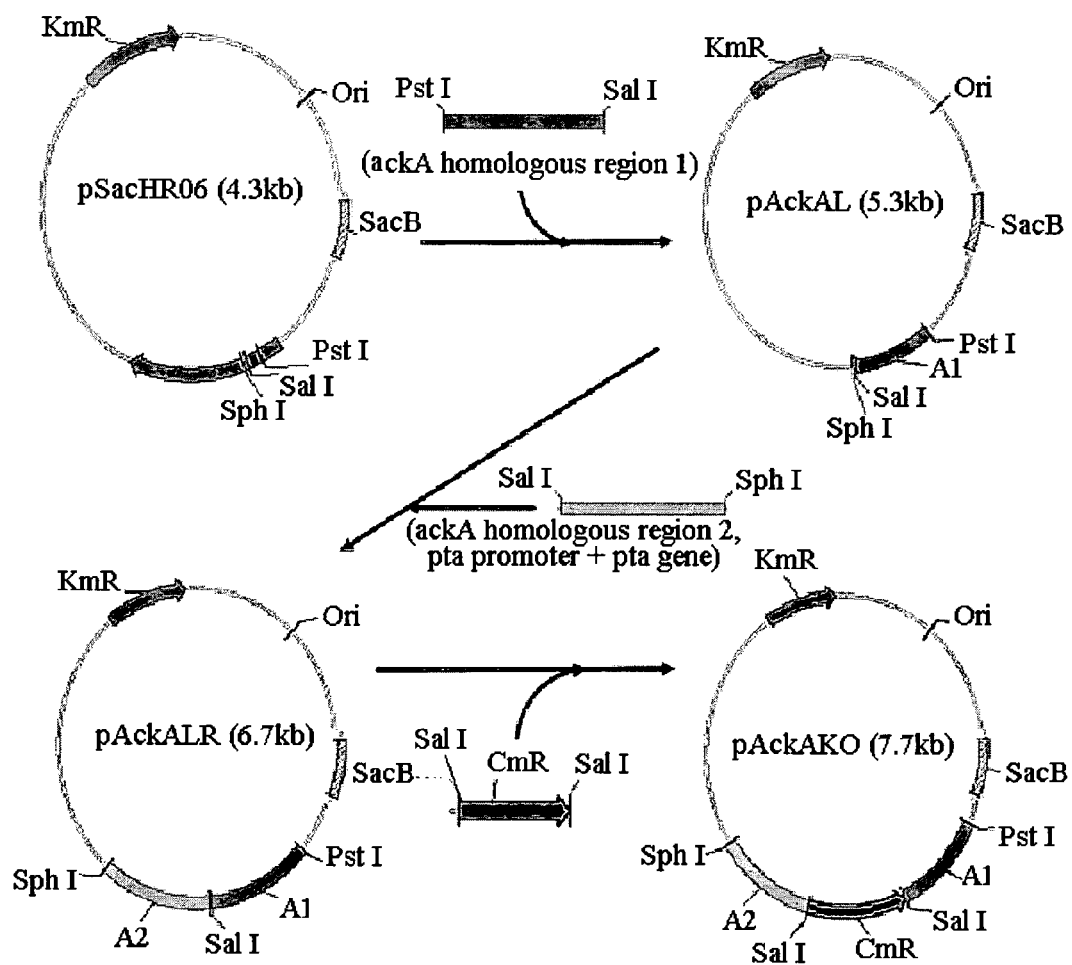
FIG. 7 shows a process of constructing a vector for disrupting ackA (pAckAKO).

Plasmid pIC156 (Steinmetz et al., *Gene*, 142:79, 1994) containing a spectinomycin-resistant gene (GenBank X02588), as a template, was subjected to PCR using primers set forth in SEQ ID NO: 30 and SEQ ID NO: 31, and the resulting PCR fragment containing a spectinomycin-resistant gene was cut with EcoRV and introduced into the pUC19-PTA12, thereby constructing pUC19-PTA 1 S2 having a spectinomycin-resistant gene. The constructed pUC19-PTA 1 S2 was cut with SacI and BamHI and inserted into the above constructed pUC19SacB, thereby constructing pPTA-sacB (FIG. 6).

```
SEQ ID NO: 30:
5'-GAATTCGAGCTCGCCCGGGGATCGATCCTC-3'

SEQ ID NO: 31:
5'-CCCGGGCCGACAGGCTTTGAAGCATGCAAATGTCAC-3'
```

Example 6

Construction of ackA-disrupted Vector (pAckAKO)

In order to disrupt an acetate kinase gene (ackA) in the genome of *M. succiniciproducens* MBEL55E by homologous recombination, a genetic exchange vector was constructed in the following manner. The genomic DNA of *M. succiniciproducens* MBEL55E, as a template, was subjected to PCR using primers set forth in SEQ ID NO: 32 and SEQ ID NO: 33. The resulting PCR product was cut with PstI and SalI and inserted into pSacHRO6 (Park et al., PNAS, 104:7797, 2007), thereby constructing pAckAL.

```
SEQ ID NO: 32:
5'-AACGACTGCAGCCACTAAATCCGACTTTGCGTAAAA-3'

SEQ ID NO: 33:
5'-AGCATGTCGACTCTTCAGGCATTGTTTGGTGGAA-3'
```

Meanwhile, the genomic DNA of *M. succiniciproducens* MBEL55E, as a template, was subjected to PCR using two sets of primers set forth in SEQ ID NO: 34 and SEQ ID NO: 35, and SEQ ID NO: 36 and SEQ ID NO: 37 for amplifying the promoter region of ackA and the forward part of pta ORF. The resulting PCR fragment was again subjected to overlapping PCR using primers set forth in SEQ ID NO: 34 and SEQ ID NO: 37, and the amplified PCR fragment was cut with SalI and SphI and inserted into pACKAL, thereby constructing pACKALR.

```
SEQ ID NO: 34:
5'-TGTGCTGTCGACTAAAGATCGCTTATCGCATGAAACTC-3'

SEQ ID NO: 35:
5'-AGGATAATTGTACGTGACATTGAACGAATAGACGTTTG
GGAATGT-3'

SEQ ID NO: 36:
5'-CCCAAACGTCTATTCGTTCAATGTCACGTACAATTATCC
TTATTCCAATC-3'

SEQ ID NO: 37:
5'-GCACATAGCATGCGTTTGCCAAGTGTTACCTTCAATAC G-3'
```

Then, pACYC184 as a template was subjected to PCR using primers set forth in SEQ ID NO: 38 and SEQ ID NO: 39, and then the resulting PCR fragment was cut with SalI and introduced into pAckALR, thereby constructing pAckAKO.

```
SEQ ID NO: 38:
5'-ATACATCGTCGACCAGGCATTTGAGAAGCACACGGT-3'

SEQ ID NO: 39:
5'-ATACGGTCGACATAAATACCTGTGACGGAAGATC-3'
```

Example 7

Construction of *M. succiniciproducens* PALK Strain

Figure 8:
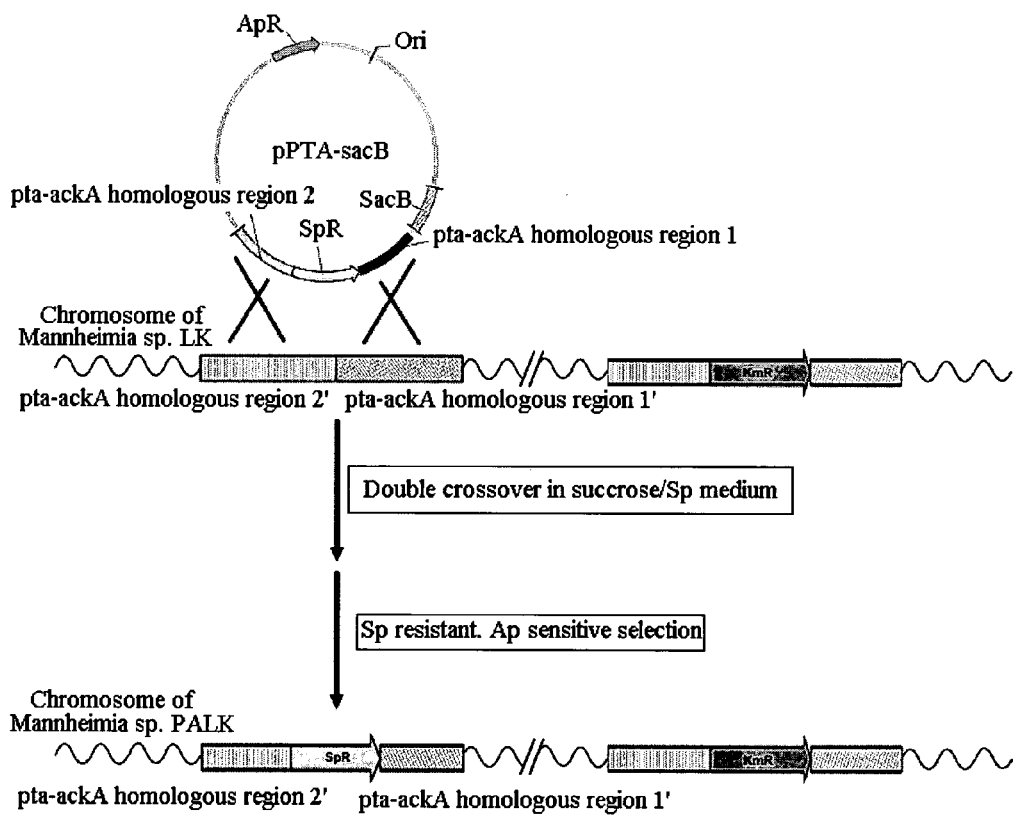
FIG. 8 shows a process of constructing a microbial variant (M succinicproducens PALK) by disrupting pta-ackA in *M. succiniciproducens* LK.

A microbial variant (*M. succiniciproducens* PALK) was constructed by disrupting pta and ackA genes in the genome of *M. succiniciproducens* LK constructed in Example 3 (FIG. 8).

*M. succiniciproducens* LK was plated on LB-glucose agar medium containing 10 g/L of glucose, and cultured at 37° C. for 36 hours. The colony formed was inoculated in 10 ml of LB-glucose liquid medium, and cultured for 12 hours. 1% (v/v) of the culture broth, which had been sufficiently grown, was inoculated in 100 ml of LB-glucose liquid medium, and cultured in a shaking incubator at 200 rpm and 37° C.

Cell concentrate was collected from the resulting culture broth in the same manner as described in Example 2, and mixed with the genetic exchange vector pPTA-sacB constructed in Examples 5, and then pPTA-sacB was introduced into *M. succiniciproducens* LK by electroporation under conditions of 2.5 kV, 50 μF and 200 ohms. 0.8 ml of LB-glucose liquid medium was added to the pPTA-sacB-introduced strain, and the strain was precultured in a thermostat at 37° C. for one and a half hour.

In order to induce a double crossover, the culture broth was plated on TSB-sucrose solid medium containing 100 g/L of sucrose(Becton, Dickinson and Company) containing spectinomycin (final concentration of 50 μg/ml) and cultured at 37° C. for 48 hours or more. In order to screen colonies where only double crossover occurred, the colonies formed were streaked on TSB-sucrose medium containing 50 μg/ml spectinomycin and TSB agar medium containing 50 μg/ml ampicillin, respectively, and cultured at 37° C. for 12 hours. Then, the colonies, which were formed on the TSB-sucrose medium containing 50 μg/ml spectinomycin but not formed on the TSB medium containing 50 μg/ml ampicillin, were selected and streaked again on the TSB-sucrose medium containing 50 μg/ml spectinomycin. The colonies formed herein were screened again using the spectinomycin-containing medium and the ampicillin-containing medium, and then the colonies which showed desired results were selected ultimately. The isolated mutant genomic DNA, as a template, was amplified by PCR, and the PCR product was electrophoresed to confirm the disruption of pta-ackA.

In order to confirm the disruption of pta-ackA, PCRs were performed twice in the following manner. First, the mutant genomic DNA, as a template, was subjected to PCR using primers set forth in SEQ ID NO: 40 and SEQ ID NO: 41. Then, the mutant genomic DNA, as a template, was subjected to PCR using primers set forth in SEQ ID NO: 42 and SEQ ID NO: 43.

```
SEQ ID NO: 40:
5'-CCTGCAGGCATGCAAGCTTGGGCTGCAGGTCGACTC-3'

SEQ ID NO: 41:
5'-GCTGCCAAACAACCGAAAATACCGCAATAAACGGC-3'

SEQ ID NO: 42:
5'-GCATGTAACTTTACTGGATATAGCTAGAAAAGGCATC
GGGGAG-3'
```

-continued

```
SEQ ID NO: 43:
5'-GCAACGCGAGGGTCAATACCGAAGGATTTCGCCG-3'
```

The products obtained in the two PCRs were subjected to gel electrophoresis to confirm the disruption of pta-ackA by their size. A microbial variant, *M. succiniciproducens* PALK was constructed by the disruption of pta-ackA from the genome of *M. succiniciproducens* LK as the above-described method.

Example 8

Construction of pta-expression Vector (pME18PTA) for Constructing *M. succiniciproducens* ALKt Strain To express a pta gene in a microbial variant lacking a lactate dehydrogenase gene (ldhA), a phosphotransacetylase gene (pta) and an acetate kinase gene (ackA), a gene expression vector was constructed as follows:

First, the genomic DNA of *M. succiniciproducens* MBEL55E, as a template, was subjected to PCR using primers set forth in SEQ ID NO: 44 and SEQ ID NO: 45 below, thereby constructing PTA-PRO.

```
SEQ ID NO: 44:
5'-CATCAGAGCTCCCTTTGCCAACAAATCCGCTAAAT-3'

SEQ ID NO: 45:
5'-AGGATAATTGTACGTGACATTGAACGAATAGACGTTTG
GGAATGT-3'
```

Next, the genomic DNA of *M. succiniciproducens* MBEL55E, as a template, was subjected to PCR using primers set forth in SEQ ID NO: 46 and SEQ ID NO: 47 below, thereby constructing PTA-GENE.

```
SEQ ID NO: 46:
5'-CCCAAACGTCTATTCGTTCAATGTCACGTACAATTATC
CTTATTCCAAT C-3'
SEQ ID NO: 47:
5'-CTACAGCCCGGGAGATCACAAAATGAAAAACTACTAT
TTGCAGG-3'
```

Figure 10:
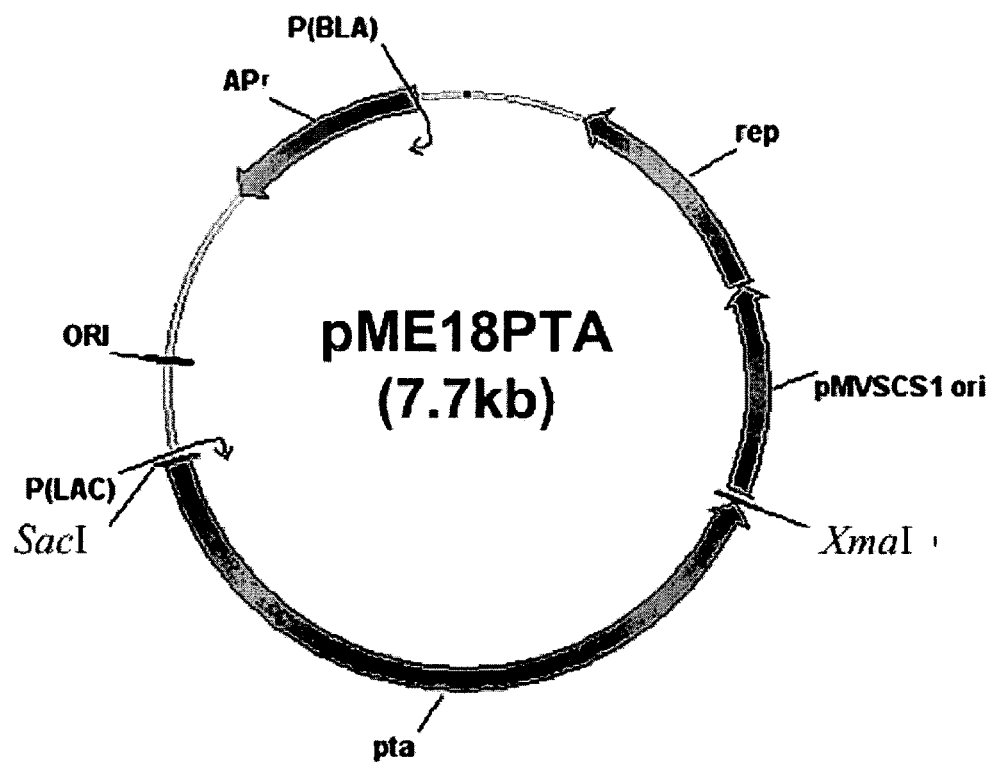
FIG. 10 is a schematic diagram showing pta expression vector (pME18PTA) used for preparing a microbial variant (*M. succinicproducens* ALKt) by expressing pta in *M. succinicproducens* PALK.

Then, PTA-PRO and PTA-GENE as templates were subjected to PCR using primers set forth in SEQ ID NO: 44 and SEQ ID NO: 47, and the resulting PCR fragment was cut with SacI and XmaI and inserted into a shuttle vector pME18, thereby constructing pME18PTA (FIG. 10).

Example 9

Construction of *M. succiniciproducens* ALKt Strain

*M. succiniciproducens* PALK constructed in Example 7 was plated on LB-glucose agar medium containing 10 g/L of glucose, and cultured at 37° C. for 36 hours. The colony formed was inoculated in 10 ml of LB-glucose liquid medium, and cultured for 12 hours. 1% (v/v) of the culture broth, which had been sufficiently grown, was inoculated in 100 ml of LB-glucose liquid medium, and cultured in a shaking incubator at 37° C. Cell concentrate was collected from said culture broth in the same manner as described in Example 2 and mixed with the pta gene expression vector pME18PTA constructed in Examples 8, and then pME18PTA was introduced into the *M. succiniciproducens* PALK by electroporation under the condition of 2.5 kV, 50 μF and 200 ohms. After electroporation, 0.8 ml of LB-glucose liquid medium was added to the pME18PTA-introduced strain, and precultured in a thermostat at 37° C. for one and a half hour.

The culture broth was plated on Tryptic Soy Broth solid medium (Becton, Dickinson and Company) containing an antibiotic ampicillin (final concentration of 50 μg/ml) and cultured at 37° C. for 48 hours or more. The colonies formed were inoculated in TSB liquid medium and cultured for more than 12 hours at 37° C. To confirm whether the vector is successfully introduced, vector was separated from the cultured strain by using GeneAll® Plasmid SV (GeneAll Biotechnology, Korea). Using primers set forth in SEQ ID NOs: 48~62 below, sequence analysis was performed by Solgent (Korea).

```
SEQ ID NO: 48:
5'-TTAGCCTGCAAATAGTAGTT-3'
SEQ ID NO: 49:
5'-CCCCGCCGATATAGTTTTAA-3'
SEQ ID NO: 50:
5'-GAAGCCGATTTCACAACCTC-3'
SEQ ID NO: 51:
5'-CTAATTTACTTGGTGTGGTT-3'
SEQ ID NO: 52:
5'-GGCGGTTACAAAATAGATTG-3'
SEQ ID NO: 53:
5'-AAGACGTAAAACGTGTTGCC-3'
SEQ ID NO: 54:
5'-ATCTGCGGAATCGGCGAAAT-3'
SEQ ID NO: 55:
5'-GGCAATTCAGGCGACACAAT-3'
SEQ ID NO: 56:
5'-CGCATAAAAATACCGCACTT-3'
SEQ ID NO: 57:
5'-TCACTTTTTCAACATCTGCG-3'
SEQ ID NO: 58:
5'-AACGAGCGACATAGTTTTCA-3'
SEQ ID NO: 59:
5'-TGCCAAGTGTTACCTTCAAT-3'
SEQ ID NO: 60:
5'-GGGCTGTTTTCAAATAGTTTGT-3'
SEQ ID NO: 61:
5'-ATAACAGGTTCGGTAGTTTC-3'
SEQ ID NO: 62:
5'-GCGATCTTTAAAACAGGATA-3'
```

Example 10

Construction of *M. succiniciproducens* ALK Strain

Figure 9:
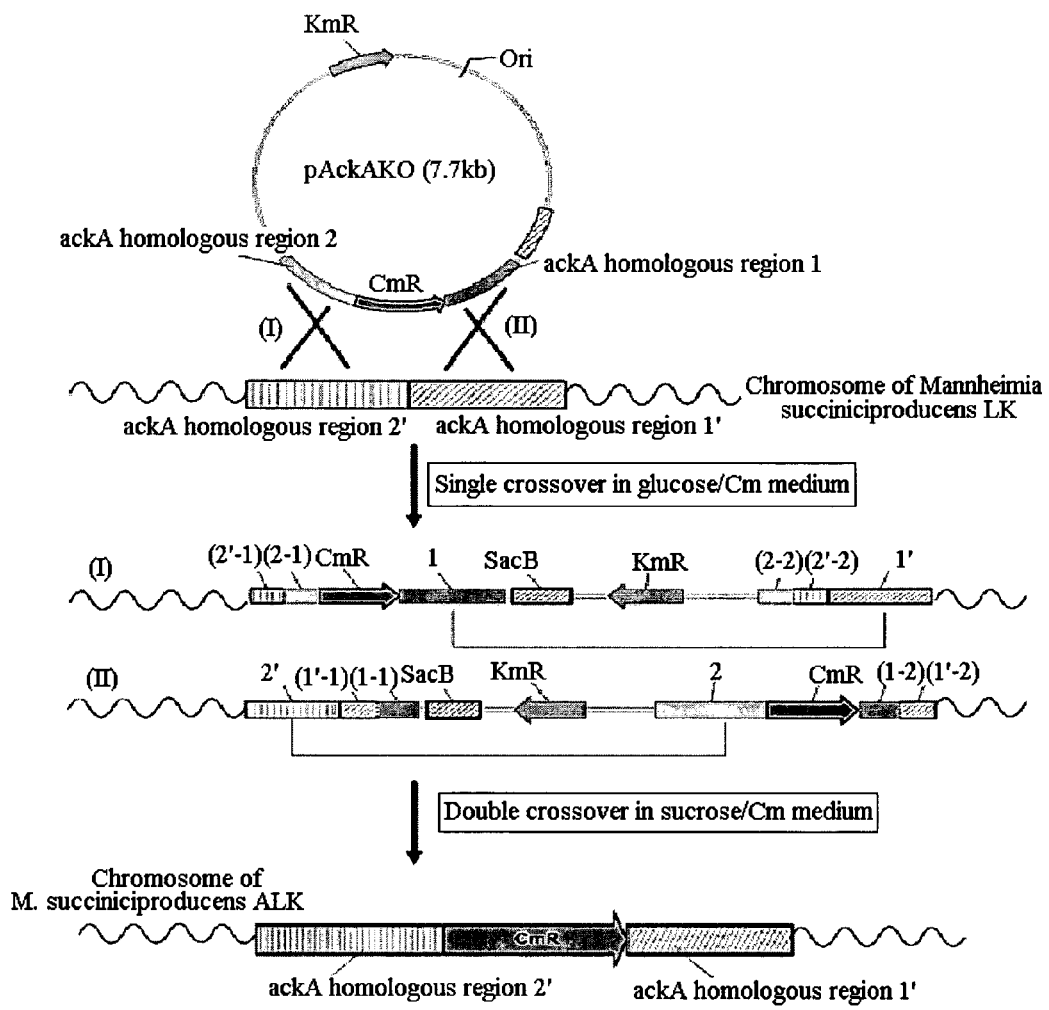
FIG. 9 shows a process of constructing a microbial variant (M succinicproducens ALK) by disrupting ackA in *M. succiniciproducens* MFLK.

A microbial variant (*M. succiniciproducens* ALK, deposited under KCTC accession no. KCTC 12326BP) was constructed by disrupting ackA gene in the genome of *M. succiniciproducens* MFLK constructed in Example 4 (FIG. 9).

*M. succiniciproducens* MFLK was plated on TBS-glucose agar medium containing 10 g/L of glucose, and cultured at 37° C. for 36 hours. The colony formed was inoculated in 10 ml of TSB-glucose liquid medium, and cultured for 12 hours. 1% (v/v) of the culture broth, which had been sufficiently grown, was inoculated in 100 ml of TSB-glucose liquid medium, and cultured in a shaking incubator at 37° C.

Cell concentrate was collected from said culture broth in the same manner as described in Example 2 and mixed with the genetic exchange vector pAckAKO constructed in Examples 6, and then pAckAKO was introduced into the *M. succiniciproducens* MFLK by electroporation under conditions of 2.5 kV, 25 μF and 400 ohms. After electroporation, 0.8 ml of LB-glucose liquid medium was added to the pAckAKO-introduced strain, and precultured in a thermostat at 37° C. for an hour.

In order to induce double crossover, the culture broth was plated on TSB-sucrose solid medium containing chloramphenicol (final concentration of 6.8 µg/ml) and cultured at 37° C. for 48 hours or more. In order to screen colonies where only double crossover occurred, the colonies formed were streaked on TSA-sucrose medium (TSA medium containing 100 g/L of sucrose) containing chloramphenicol (final concentration of 6.8 µg/ml). 24 hours later, colonies formed were again streaked on the same plate. Using colonies obtained by repeating the above process, PCR was performed and the resulting PCR product was electrophoresed to confirm the disruption of ackA.

In order to confirm the disruption of ackA, PCRs were performed twice in the following manner. First, the mutant genomic DNA, as a template, was subjected to PCR using primers set forth in SEQ ID NO: 63 and SEQ ID NO: 64. Then, the mutant genomic DNA, as a template, was subjected to PCR using primers set forth in SEQ ID NO: 65 and SEQ ID NO: 66.

```
SEQ ID NO: 63:
5'-CGCTAAATGCTGATAGGTTGGGC-3'
SEQ ID NO: 64:
5'-CCCAATGGCATCGTAAAGAACA-3'
SEQ ID NO: 65:
5'-GGAAGCCAGTGAATGAATGAAAT-3'
SEQ ID NO: 66:
5'-ACATGGAAGCCATCACAGACGG-3'
```

The products obtained by the two PCRs were subjected to gel electrophoresis to confirm the disruption of ackA by their size. A microbial variant, *M. succiniciproducens* ALK was constructed by the disruption of ackA from the genome of a microbial variant *M. succiniciproducens* MFLK as the above-described method.

Example 11

Production of Homo-succinic Acid Using *M. succiniciproducens* ALKt and ALK Strains

*M. succiniciproducens* ALKt constructed in Example 9 and *M. succiniciproducens* ALK constructed in Example 10 were plated in 10 ml of composition medium containing 5 g/L of glucose, respectively, and cultured in anaerobic conditions at 39° C. for 8 hours, and then moved to 250 ml of composition medium containing 5 g/L of glucose and cultured at 39° C. At this time, 50 µg/ml ampicillin was added to the medium for culturing *M. succiniciproducens* ALKt and 6.8 µg/ml chloramphenicol to the medium for culturing *M. succiniciproducens* ALK. Each 250 ml of the culture broth of *M. succiniciproducens* ALKt and *M. succiniciproducens* ALK was inoculated in a bioreactor containing 2.25 L of composition medium (1 g/L of NaCl, 2 g/L of $(NH_4)_2HPO_4$, 0.02 g/L of $CaCl_2.2H_2O$, 0.2 g/L of $MgCl_2.6H_2O$, 8.709 g/L of $K_2HPO_4$, 0.5 g/L of cystein, 0.5 g/L of methionine, 0.5 g/L of alanine, 0.5 g/L of asparagines, 0.5 g/L of aspartic acid, 0.5 g/L of praline, 0.5 g/L of serine, 0.005 g/L of nicotinic acid, 0.005 g/L of Ca-pantothenate, 0.005 g/L of pyridoxine.HCl, 0.005 g/L of thiamine, 0.005 g/L of ascorbic acid, and 0.005 g/L of biotin), and the fermentation was performed under conditions of an initial glucose concentration of 100 mM, at 39° C. During the fermentation, the pH of the culture was adjusted to 6.5 by using ammonia solution, and the concentrations of ampicillin and chloramphenicol, used as an antibiotic, were the same as that mentioned above.

The concentration of cells in the culture broth was measured with a spectrophotometer, and then calculated using the previously measured optical density of spectrophotometer and the verification test for dried-cell weight. During the fermentation, samples were collected from the bioreactor regularly. The collected samples were centrifuged at 13,000 rpm for 10 minutes, and then the supernatants were used to analyze the concentrations of glucose and various metabolites, including succinic acid and other organic acids and ethanol by using a High-Performance Liquid Chromatography.

Figure 11:
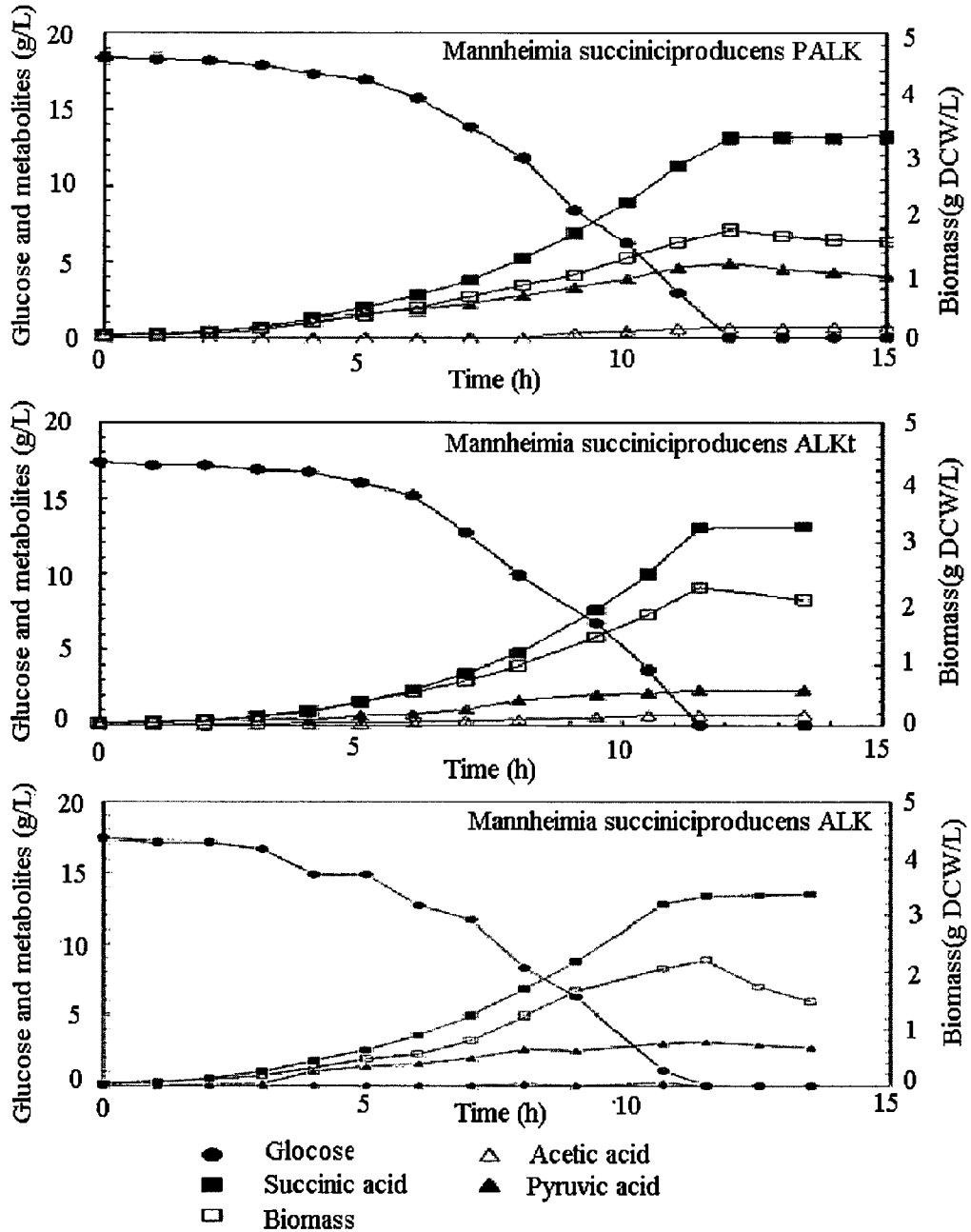
FIG. 11 shows the culture characteristics of the inventive *M. succiniciproducens* PALK, *M. succiniciproducens* ALKt and *M. succiniciproducens* ALK in anaerobic conditions saturated with $CO_2$.

As shown in FIG. 11 and Table 1, genetically engineered *M. succiniciproducens* ALKt and *M. succiniciproducens* ALK showed excellent succinic acid productivity and remarkably suppressed byproduct formation. *M. succiniciproducens* ALKt strain showed increases of 61.7% and 7.0% in the yields of succinic acid per gram of glucose, respectively, compared with its parent strains *M. succiniciproducens* MBEL55E and *M. succiniciproducens* PALK, and *M. succiniciproducens* ALK strain showed increases of 63.8% and 8.5% in the yields of succinic acid per gram of glucose, respectively, compared with its parent stains *M. succiniciproducens* MBEL55E and *M. succiniciproducens* PALK. On the contrary, *M. succiniciproducens* ALKt and *M. succiniciproducens* ALK reduced byproduct formation by 54.1% and 43.4% compared with *M. succiniciproducens* MBEL55E and *M. succiniciproducens* PALK, which makes it possible to save an enormous amount of raw material and reduce costs for succinic acid separation and purification. Additionally, the final cell concentration of *M. succiniciproducens* ALKt strain was 2.29 g/L and that of *M. succiniciproducens* ALK strain was 2.22 g/L, which are increases in the final cell concentration by 29.3% and 28.4%, respectively, compared to *M. succiniciproducens* PALK, indicating improvement of cell growth.

TABLE 1

| Succinic acid productivity of *M. succiniciproducens* ALKt and ALK | | | | |
|---|---|---|---|---|
| Strain | MBEL55E | PALK | ALKt | ALK |
| Final succinic acid conc. (g/L) | 10.49 | 13.17 | 13.11 | 13.36 |
| Glucose consumption (g/L) | 22.50 | 18.45 | 17.33 | 17.45 |
| Succinic acid yield (g succinic acid/g glucose) | 0.47 | 0.71 | 0.76 | 0.77 |
| Increase of succinic acid yield to wild type strain (MBEL55E) (%) | 0 | +51.1 | +61.7 | +63.8 |
| Final byproduct conc. (g/L) | 8.43 | 5.6 | 3.03 | 2.93 |
| Byproduct yield (g byproduct/g glucose) | 0.37 | 0.30 | 0.17 | 0.17 |
| Decrease of byproduct yield to wild type strain (MBEL55E) (%) | 0.00 | 18.9 | −54.1 | −54.1 |

INDUSTRIAL APPLICABILITY

As described and proved above in detail, the present invention has an effect to provide methods for constructing microbial variants producing homo-succinic acid at a high concentration, and methods for producing high yields of homo-succinic acid using the same. Both *M. succiniciproducens* ALKt and *M. succiniciproducens* ALK according to the present invention effectively suppress various organic acids formed as a byproduct during the production of succinic acid by microorganism fermentation. Thus, the inventive microbial variants are useful to produce succinic acid at high yields for industrial use.

While the present invention has been described in detail with reference to the specific features, it will be apparent to persons skilled in the art that this description is only for a preferred embodiment and does not limit the scope of the present invention. Thus, the substantial scope of the present invention will be defined by the appended claims and equivalents thereof.

What is claimed is:

1. A succinic acid-producing microbial variant lacking a lactate dehydrogenase gene (ldhA) and an acetate kinase gene (ackA) while maintaining a phosphotransacetylase gene (pta), which is capable of producing succinic acid at high concentration in anaerobic conditions,
  wherein the succinic acid-producing microbial variant is selected from the group consisting of *Actinobacillus* sp., *Anaerobiospirillum* sp., and *Mannheimia* sp. and wherein said succinic acid-producing microbial variant is *Mannheimia succiniciproducens* ALK, whose accession number is KCTC 12326BP wherein a lactate dehydrogenase gene (ldhA) and an acetate kinase gene (ackA) are disrupted in said variant.

2. The succinic acid-producing microbial variant according to claim 1, wherein the microbial variant producing succinic acid is a homo-fermentative microorganism producing homo-succinic acid at high yields without the accumulation of other organic acids as byproducts.

3. A method for producing a succinic acid-producing microbial variant of claim 1, the method comprising the steps of:
  (a) obtaining a succinic acid-producing microbial variant lacking a gene encoding lactate dehydrogenase (ldhA) by disrupting a gene encoding lactate dehydrogenase gene (ldhA) in the genome of a succinic acid-producing microorganism by homologous recombination,
  wherein the succinic acid-producing microbial variant is selected from the group consisting of *Actinobacillus* sp., *Anaerobiospirillum* sp. and *Mannheimia* sp. and wherein said succinic acid-producing microbial variant is *Mannheimia succiniciproducens* ALK, whose accession number is KCTC 12326BP wherein a lactate dehydrogenase gene (ldhA) and an acetate kinase gene (ackA) are disrupted in said variant; and
  (b) obtaining a succinic acid-producing microbial variant lacking a gene encoding lactate dehydrogenase (ldhA) and a gene encoding acetate kinase (ackA) by disrupting a gene encoding acetate kinase (ackA) in the genome of the succinic acid-producing microbial variant lacking a gene encoding lactate dehydrogenase (ldhA) by homologous recombination.

4. The method for producing the succinic acid-producing microbial variant according to claim 3, wherein said homologous recombination is performed by using a genetic exchange vector containing a disrupted ldhA and a genetic exchange vector containing a disrupted ackA.

5. The method for producing the succinic acid-producing microbial variant according to claim 4, wherein said genetic exchange vectors containing a disrupted ldhA is pMLKO-SacB and pMFldhA, and said genetic exchange vectors containing a disrupted ackA is pMLKO-sacB and pAckAKO.

6. A method for constructing the succinic acid-producing microbial variant of claim 1, which comprises introducing a gene encoding phosphotransacetylase (pta) into a succinic acid-producing microbial variant lacking a lactate dehydrogenase gene (ldhA), a phosphotransacetylase gene (pta) and a acetate kinase gene (ackA).

7. A method for producing succinic acid, the method comprising the steps of culturing the succinic acid-producing microbial variant of claim 1 in anaerobic conditions; and recovering succinic acid from the culture broth.

8. The method for producing succinic acid according to claim 7, wherein glucose is used as a carbon source for the culture.

* * * * *

SEQUENCE LISTING

<160> NUMBER OF SEQ ID NOS: 66

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
cagtgaagga gctccgtaac gcatccgccg                                       30

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
ctttatcgaa tctgcaggcg gtttccaaaa                                       30

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
gtactgtaaa ctgcagcttt catagttagc                                       30

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
gccgaaagtc aagcttgccg tcgtttagtg                                       30

<210> SEQ ID NO 5
<211> LENGTH: 10
<212> TYPE: DNA
<213> ORGANISM: Artificial
<220> FEATURE:
<223> OTHER INFORMATION: linker

<400> SEQUENCE: 5
tctagaagct                                                             10

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
gctctagacc ttctatcgcc ttcttgacg                                        29

<210> SEQ ID NO 7
<211> LENGTH: 29
<212> TYPE: DNA
<213> ORGANISM: Artificial

<220> FEATURE:
<223> OTHER INFORMATION: primer

<400> SEQUENCE: 7
gctctagagg ctacaaaatc acgggcgtc                29

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
ttgcaacatg gcgaacttag c                        21

<210> SEQ ID NO 9
<211> LENGTH: 29
<212> TYPE: DNA
<213> ORGANISM: Artificial
<220> FEATURE:
<223> OTHER INFORMATION: primer

<400> SEQUENCE: 9
atatctgcag ttaataaaat gcgcgacgg                29

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
atatgtcgac caactttcat agttagctcc               30

<210> SEQ ID NO 11
<211> LENGTH: 29
<212> TYPE: DNA
<213> ORGANISM: Artificial
<220> FEATURE:
<223> OTHER INFORMATION: primer

<400> SEQUENCE: 11
atccgcatgc ttgccgtcgt ttagtgctg                29

<210> SEQ ID NO 12
<211> LENGTH: 63
<212> TYPE: DNA
<213> ORGANISM: Artificial
<220> FEATURE:
<223> OTHER INFORMATION: primer

<400> SEQUENCE: 12
atataagctt taccgttcgt atagcataca ttatacgaag ttatgacggg ctggcggtat    60
tgg                                                                 63

<210> SEQ ID NO 13
<211> LENGTH: 64
<212> TYPE: DNA
<213> ORGANISM: Artificial
<220> FEATURE:
<223> OTHER INFORMATION: primer

<400> SEQUENCE: 13

```
aattcccggg taccgttcgt ataatgtatg ctatacgaag ttattgccag ttgatcacct    60
cggg                                                                 64

<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14
gacgtttccc gttgaatatg gc                                             22

<210> SEQ ID NO 15
<211> LENGTH: 24
<212> TYPE: DNA
<213> ORGANISM: Artificial
<220> FEATURE:
<223> OTHER INFORMATION: primer

<400> SEQUENCE: 15
cattgaggcg tattatcagg aaac                                           24

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
gcagtttcat ttgatgctcg atg                                            23

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
cctcttacga tgacgcatct ttcc                                           24

<210> SEQ ID NO 18
<211> LENGTH: 22
<212> TYPE: DNA
<213> ORGANISM: Artificial
<220> FEATURE:
<223> OTHER INFORMATION: primer

<400> SEQUENCE: 18
acctttacta ccgcactgct gg                                             22

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
gcgggagtca gtgaacaggt ac                                             22

<210> SEQ ID NO 20
```

```
<211> LENGTH: 22
<212> TYPE: DNA
<213> ORGANISM: Artificial
<220> FEATURE:
<223> OTHER INFORMATION: primer

<400> SEQUENCE: 20
ttacagctca ccgaaagcac gc                                           22

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
ataagcggcg ttaaccttca ac                                           22

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
ttacagctca ccgaaagcac gc                                           22

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
aattcgtaac gcatccgccg                                              20

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
agcggatccc cttctatcgc cttcttgacg                                   30

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
gtcctgcagg gctacaaaat cacgggcgtc                                   30

<210> SEQ ID NO 26
<211> LENGTH: 32
<212> TYPE: DNA
<213> ORGANISM: Artificial
<220> FEATURE:
<223> OTHER INFORMATION: primer

<400> SEQUENCE: 26
```

```
gctctagata tccgcagtat cactttctgc gc                               32
```

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27

```
tccgcagtcg gatccgggtt aaccgcacag                                  30
```

<210> SEQ ID NO 28
<211> LENGTH: 39
<212> TYPE: DNA
<213> ORGANISM: Artificial
<220> FEATURE:
<223> OTHER INFORMATION: primer

<400> SEQUENCE: 28

```
ggggagctcg ctaacttagc ttctaaaggc catgtttcc                        39
```

<210> SEQ ID NO 29
<211> LENGTH: 32
<212> TYPE: DNA
<213> ORGANISM: Artificial
<220> FEATURE:
<223> OTHER INFORMATION: primer

<400> SEQUENCE: 29

```
gctctagata tccgggtcaa tatcgccgca ac                               32
```

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30

```
gaattcgagc tcgcccgggg atcgatcctc                                  30
```

<210> SEQ ID NO 31
<211> LENGTH: 36
<212> TYPE: DNA
<213> ORGANISM: Artificial
<220> FEATURE:
<223> OTHER INFORMATION: primer

<400> SEQUENCE: 31

```
cccgggccga caggctttga agcatgcaaa tgtcac                           36
```

<210> SEQ ID NO 32
<211> LENGTH: 36
<212> TYPE: DNA
<213> ORGANISM: Artificial
<220> FEATURE:
<223> OTHER INFORMATION: primer

<400> SEQUENCE: 32

```
aacgactgca gccactaaat ccgactttgc gtaaaa                           36
```

<210> SEQ ID NO 33
<211> LENGTH: 34
<212> TYPE: DNA

<213> ORGANISM: Artificial
<220> FEATURE:
<223> OTHER INFORMATION: primer

<400> SEQUENCE: 33
agcatgtcga ctcttcaggc attgtttggt ggaa          34

<210> SEQ ID NO 34
<211> LENGTH: 38
<212> TYPE: DNA
<213> ORGANISM: Artificial
<220> FEATURE:
<223> OTHER INFORMATION: primer

<400> SEQUENCE: 34
tgtgctgtcg actaaagatc gcttatcgca tgaaactc          38

<210> SEQ ID NO 35
<211> LENGTH: 45
<212> TYPE: DNA
<213> ORGANISM: Artificial
<220> FEATURE:
<223> OTHER INFORMATION: primer

<400> SEQUENCE: 35
aggataattg tacgtgacat tgaacgaata gacgtttggg aatgt          45

<210> SEQ ID NO 36
<211> LENGTH: 50
<212> TYPE: DNA
<213> ORGANISM: Artificial
<220> FEATURE:
<223> OTHER INFORMATION: primer

<400> SEQUENCE: 36
cccaaacgtc tattcgttca atgtcacgta caattatcct tattccaatc          50

<210> SEQ ID NO 37
<211> LENGTH: 39
<212> TYPE: DNA
<213> ORGANISM: Artificial
<220> FEATURE:
<223> OTHER INFORMATION: primer

<400> SEQUENCE: 37
gcacatagca tgcgtttgcc aagtgttacc ttcaatacg          39

<210> SEQ ID NO 38
<211> LENGTH: 36
<212> TYPE: DNA
<213> ORGANISM: Artificial
<220> FEATURE:
<223> OTHER INFORMATION: primer

<400> SEQUENCE: 38
atacatcgtc gaccaggcat ttgagaagca cacggt          36

<210> SEQ ID NO 39
<211> LENGTH: 34
<212> TYPE: DNA
<213> ORGANISM: Artificial
<220> FEATURE:
<223> OTHER INFORMATION: primer

<400> SEQUENCE: 39
atacggtcga cataaatacc tgtgacggaa gatc          34

```
<210> SEQ ID NO 40
<211> LENGTH: 36
<212> TYPE: DNA
<213> ORGANISM: Artificial
<220> FEATURE:
<223> OTHER INFORMATION: primer

<400> SEQUENCE: 40
cctgcaggca tgcaagcttg ggctgcaggt cgactc                          36

<210> SEQ ID NO 41
<211> LENGTH: 35
<212> TYPE: DNA
<213> ORGANISM: Artificial
<220> FEATURE:
<223> OTHER INFORMATION: primer

<400> SEQUENCE: 41
gctgccaaac aaccgaaaat accgcaataa acggc                           35

<210> SEQ ID NO 42
<211> LENGTH: 43
<212> TYPE: DNA
<213> ORGANISM: Artificial
<220> FEATURE:
<223> OTHER INFORMATION: primer

<400> SEQUENCE: 42
gcatgtaact ttactggata tagctagaaa aggcatcggg gag                  43

<210> SEQ ID NO 43
<211> LENGTH: 34
<212> TYPE: DNA
<213> ORGANISM: Artificial
<220> FEATURE:
<223> OTHER INFORMATION: primer

<400> SEQUENCE: 43
gcaacgcgag ggtcaatacc gaaggatttc gccg                            34

<210> SEQ ID NO 44
<211> LENGTH: 35
<212> TYPE: DNA
<213> ORGANISM: Artificial
<220> FEATURE:
<223> OTHER INFORMATION: primer

<400> SEQUENCE: 44
catcagagct ccctttgcca acaaatccgc taaat                           35

<210> SEQ ID NO 45
<211> LENGTH: 45
<212> TYPE: DNA
<213> ORGANISM: Artificial
<220> FEATURE:
<223> OTHER INFORMATION: primer

<400> SEQUENCE: 45
aggataattg tacgtgacat tgaacgaata gacgtttggg aatgt                45

<210> SEQ ID NO 46
<211> LENGTH: 50
<212> TYPE: DNA
<213> ORGANISM: Artificial
<220> FEATURE:
```

<223> OTHER INFORMATION: primer

<400> SEQUENCE: 46
cccaaacgtc tattcgttca atgtcacgta caattatcct tattccaatc        50

<210> SEQ ID NO 47
<211> LENGTH: 44
<212> TYPE: DNA
<213> ORGANISM: Artificial
<220> FEATURE:
<223> OTHER INFORMATION: primer

<400> SEQUENCE: 47
ctacagcccg ggagatcaca aaatgaaaaa ctactatttg cagg              44

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ttagcctgca aatagtagtt                                         20

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
ccccgccgat atagttttaa                                         20

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
gaagccgatt tcacaacctc                                         20

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
ctaatttact tggtgtggtt                                         20

<210> SEQ ID NO 52
<211> LENGTH: 20
<212> TYPE: DNA
<213> ORGANISM: Artificial
<220> FEATURE:
<223> OTHER INFORMATION: primer

```
<400> SEQUENCE: 52
ggcggttaca aaatagattg                                          20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
aagacgtaaa acgtgttgcc                                          20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
atctgcggaa tcggcgaaat                                          20

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
ggcaattcag gcgacacaat                                          20

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
cgcataaaaa taccgcactt                                          20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
tcactttttc aacatctgcg                                          20

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
aacgagcgac atagttttca                                          20

<210> SEQ ID NO 59
```

```
<211> LENGTH: 20
<212> TYPE: DNA
<213> ORGANISM: Artificial
<220> FEATURE:
<223> OTHER INFORMATION: primer

<400> SEQUENCE: 59
tgccaagtgt taccttcaat                                              20

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
gggctgtttt caaatagttt gt                                           22

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
ataacaggtt cggtagtttc                                              20

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
gcgatcttta aaacaggata                                              20

<210> SEQ ID NO 63
<211> LENGTH: 23
<212> TYPE: DNA
<213> ORGANISM: Artificial
<220> FEATURE:
<223> OTHER INFORMATION: primer

<400> SEQUENCE: 63
cgctaaatgc tgataggttg ggc                                          23

<210> SEQ ID NO 64
<211> LENGTH: 22
<212> TYPE: DNA
<213> ORGANISM: Artificial
<220> FEATURE:
<223> OTHER INFORMATION: primer

<400> SEQUENCE: 64
cccaatggca tcgtaaagaa ca                                           22

<210> SEQ ID NO 65
<211> LENGTH: 23
<212> TYPE: DNA
<213> ORGANISM: Artificial
<220> FEATURE:
<223> OTHER INFORMATION: primer

<400> SEQUENCE: 65
```

```
ggaagccagt gaatgaatga aat                                              23

<210> SEQ ID NO 66
<211> LENGTH: 22
<212> TYPE: DNA
<213> ORGANISM: Artificial
<220> FEATURE:
<223> OTHER INFORMATION: primer

<400> SEQUENCE: 66
acatggaagc catcacagac gg                                               22
```